US011884731B2

(12) United States Patent
Lasch

(10) Patent No.: US 11,884,731 B2
(45) Date of Patent: Jan. 30, 2024

(54) VEDOLIZUMAB FOR THE TREATMENT OF FISTULIZING CROHN'S DISEASE

(71) Applicant: MILLENNIUM PHARMACEUTICALS, INC., Cambridge, MA (US)

(72) Inventor: Karen L. Lasch, Deerfield, IL (US)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 16/297,990

(22) Filed: Mar. 11, 2019

(65) Prior Publication Data
US 2020/0031937 A1 Jan. 30, 2020

Related U.S. Application Data

(63) Continuation of application No. 15/529,308, filed as application No. PCT/US2015/062705 on Nov. 25, 2015, now abandoned.

(60) Provisional application No. 62/084,815, filed on Nov. 26, 2014.

(51) Int. Cl.
A61K 39/00 (2006.01)
A61K 39/395 (2006.01)
C07K 16/28 (2006.01)
G01N 33/564 (2006.01)
G01N 33/68 (2006.01)
G01N 33/00 (2006.01)

(52) U.S. Cl.
CPC ....... C07K 16/2839 (2013.01); G01N 33/564 (2013.01); G01N 33/68 (2013.01); A61K 2039/505 (2013.01); A61K 2039/54 (2013.01); A61K 2039/545 (2013.01); C07K 2317/24 (2013.01); G01N 33/00 (2013.01); G01N 2333/70546 (2013.01); G01N 2800/065 (2013.01); G01N 2800/52 (2013.01)

(58) Field of Classification Search
None
See application file for complete search history.

(56) References Cited

U.S. PATENT DOCUMENTS

| 9,663,579 | B2 | 5/2017 | Fox et al. |
| 9,764,033 | B2 | 9/2017 | Diluzio et al. |
| 10,004,808 | B2 | 6/2018 | Fox et al. |
| 10,040,855 | B2 | 8/2018 | Diluzio et al. |
| 10,143,752 | B2 | 12/2018 | Fox et al. |

FOREIGN PATENT DOCUMENTS

| WO | 9624673 A1 | 8/1996 |
| WO | 9806248 A2 | 2/1998 |
| WO | 01/078779 A2 | 10/2001 |
| WO | 2006/136244 | 12/2006 |
| WO | 2007061679 A1 | 5/2007 |
| WO | WO2008/150490 A2 | 12/2008 |
| WO | 2012151247 A2 | 11/2012 |
| WO | 2012151248 A2 | 11/2012 |
| WO | 2013/181694 | 12/2013 |
| WO | 2016105572 A1 | 6/2016 |
| WO | 2017192867 A1 | 11/2017 |
| WO | 2017218434 A1 | 12/2017 |
| WO | 2018200818 A2 | 11/2018 |
| WO | 2018215995 A1 | 11/2018 |

OTHER PUBLICATIONS

Schwartz et al. A Comparison of Endoscopic Ultrasound, Magnetic Resonance Imaging, and Exam Under Anesthesia for Evaluation of Crohn's Perianal Fistulas. Gastroenterology 2001;121:1064-1072. (Year: 2001).*
Sostegni et al. Review article: Crohn's disease: monitoring disease activity. Aliment Pharmacol Ther 2003; 17 (Suppl. 2): 11-17. (Year: 2003).*
Raine, T., Vedolizumab for inflammatory bowel disease: Changing the game, or more of the same? United European astroenterology Journal, Jul. 2014, vol. 2(5) 333-344. (Year: 2014).*
Supplementary Appendix-Supplement to: Sandborn WJ, Feagan BG, Rutgeerts P, et al. Vedolizumab as induction and maintenance therapy for Crohn's disease. N Engl J Med 2013;369:711-21. DOI: 10.1056/NEJMoa1215739 . . . (Year: 2013).*
Sandborn et al. A Review of Activity Indices and EfÞcacy Endpoints for Clinical Trials of Medical Therapy in Adults With CrohnÕs Disease. Gastroenterology 2002;122:512-530. (Year: 2002).*
Yassin et al . Gut homing markers in perianal Crohn's fistulae. Abstract: OP015. Journal of Crohn's and Colitis, vol. 8, Issue Supplement_1, Feb. 1, 2014,p. S9. (Year: 2014).*
Yassin et al. The Role of the Gut Homing Marker (B7) in the Immunopathogenisis of Perianal Crohn's Fistulae—Increased Expression on Dendritic Cells. Abstract: P1388, United European Gastroenterology Journal 1(1S), Oct. 2013, p. A506. (Year: 2013).*
Ziman, T. L., . Vedolizumab Should be Used as a First Line Biologic in IBD. University of Washington Medical Center. pp. 1-34. (Year: 2015).*
Yassin et al. The immune cell activation and homing profile of dendritic cells in fistulating perianal crohn's disease. Gastroenterology, (May 2013) vol. 144, No. 5, Supp. Suppl. 1, pp. S318. Abstract No. Sa1843. (Year: 2013).*
Yassin et al. The aetiology, immune activation and homing profile of dendritic cells in fistulating perianal crohn's disease. Journal of Crohn's and Colitis, (Feb. 2013) vol. 7, Supp. Suppl.1, pp. S13. Abstract No. P007. (Year: 2013).*
Yassin et al. Do perianal Crohn's fistulae arise from the gut?. Colorectal Disease, (Sep. 2013) vol. 15, Supp. Suppl. 3, pp. 12. Abstract No. F36. (Year: 2013).*

(Continued)

Primary Examiner — Maher M Haddad
(74) Attorney, Agent, or Firm — Womble Bond Dickinson (US) LLP

(57) ABSTRACT

A method for treating a human patient suffering from fistulizing Crohn's disease, comprising administering to a patient suffering from fistulizing Crohn's disease, a humanized antibody having binding specificity for human α4β7 integrin, wherein the human patient has a seton that was surgically placed prior to administration of the antibody, and wherein the dosing regimen induces fistula(e) healing.

20 Claims, 3 Drawing Sheets

Specification includes a Sequence Listing.

(56) References Cited

OTHER PUBLICATIONS

Yassin et al. The aetiology of Crohn's and idiopathic anal fistulae—Are there any differences in the dendritic cells homing profile?. Colorectal Disease, (Jul. 2013) vol. 15, Supp. Suppl. 1, pp. 12. Abstract No. 48. (Year: 2013).*
Christine Richardson, What is a Crohn's disease fistula? Medically reviewed by Kelsey Trull, PA-C, pp. 1-10. Mar. 9, 2022 (Year: 2022).*
Schwartz et al. Guidelines for Medical Treatment of Crohn's Perianal Fistulas: Critical Evaluation of Therapeutic Trials. Inflamm. Bowel Dis. 21(4), 737-752, 2015. (Year: 2015).*
"Vedolizumab IV 300 mg in the Treatment of Fistulizing Crohn's Disease (Enterprise)." Clinical Trials Identifier: NCT02630966. Retrieved from clinicaltrials.gov on Jul. 29, 2020.
The International Search Report PCT/US2015/062705, dated Mar. 17, 2016.
Hotokezaka, et al., "Results of Seton Drainage and Infliximab Infusion for Complex Anal Crohn's Disease", Hepato-Gastroenterology, v. 58, No. 109, Jul. 2011, pp. 1189-1192.
Sanborn, et al., "Vedolizumab as Induction and Maintenance Therapy for Crohn's Disease", New England Journal of Medicine, v. 369, No. 8, Aug. 2013, pp. 711-721.
Sanborn, et al., "Vedolizumab as Induction and Maintenance Therapy for Crohn's Disease; Supplementary Appendix", New England Journal of Medicine, v. 369, No. 8, Aug. 2013, pp. 1-59.
European Medicines Agency: "7 Westferry Circus, Canary Wharf, London E14 4HB; United Kingdom—An agency of the European Union EPAR Summary for the public", Jun. 2014, Annex I: Summary of Product Characteristics, retrieved from the Internet: http://www.ema.europa.eu/docs/en_GB/document_library/EPAR_summary_for_the_public/human/002782/WC500168532.
European Medicines Agency: "7 Westferry Circus, Canary Wharf, London E14 4HB; United Kingdom—An agency of the European Union EPAR Summary for the public", Jun. 2014, retrieved from the internet: http://www.ema.europa.eu/docs/en_GB/document_library/EPAR_Product_Information/human/002782/WC500168528.
Sands, et al., "Effects of Vedolizumab Induction Therapy for Patients with Crohn's Disease in Whom Tumor Necrosis Factor Antagonist Treatment Failed", Gastroenterology, v. 147, No. 3, Sep. 2014, pp. 618-627.
Feagan, et al., "Vedolizumab for the Treatment of Fistulizing Crohn's Disease: An Exploratory Analysis of Data from GEMINI 2", Gastroenterology, vol. 148, No. 4, Apr. 2015, p. S274.
Schwartz et al., P476 Efficacy and safety of 2 vedolizumab IV regimens in patients with perianal fistulising Crohn's disease: results of the Enterprise study. J Crohns Colitis, vol. 14, Issue Supplement 1, Jan. 2020, p. S418.
"What Is A Fistula? Types, causes and treatments explained.—NAFC", Web page <<https://www.nafc.org/fistula>>, 5 pages, retrieved on Feb. 16, 2021.
Feagan, et al., "Efficacy of Vedolizumab in Fistulising Crohn's Disease: Exploratory Analyses of Data from GEMINI 2", J Crohns Colitis, 2018,12(5):621-626.
Ruffolo et al., "Perianal Crohn's disease: Is there something new?", World J, Gastroenterol., 2011; 17(15): 1939-1946.
Schwartz, et al. Efficacy and Safety of 2 Vedolizumab Intravenous Regimens for Perianal Fistulizing Crohn's Disease: Enterprise Study. Clin Gastroenterol Hepatol. May 2022;20(5):1059-1067.e9. doi: 10.1016/j.cgh.2021.09.028.
Luzentales-Simpson, et al. Vedolizumab: Potential Mechanisms of Action for Reducing Pathological Inflammation in Inflammatory Bowel Diseases, Frontiers in Cell and Developmental Biology. Feb. 3, 2021;vol. 9:1-10, doi: 10.3389/fcell.2021.612830.

* cited by examiner

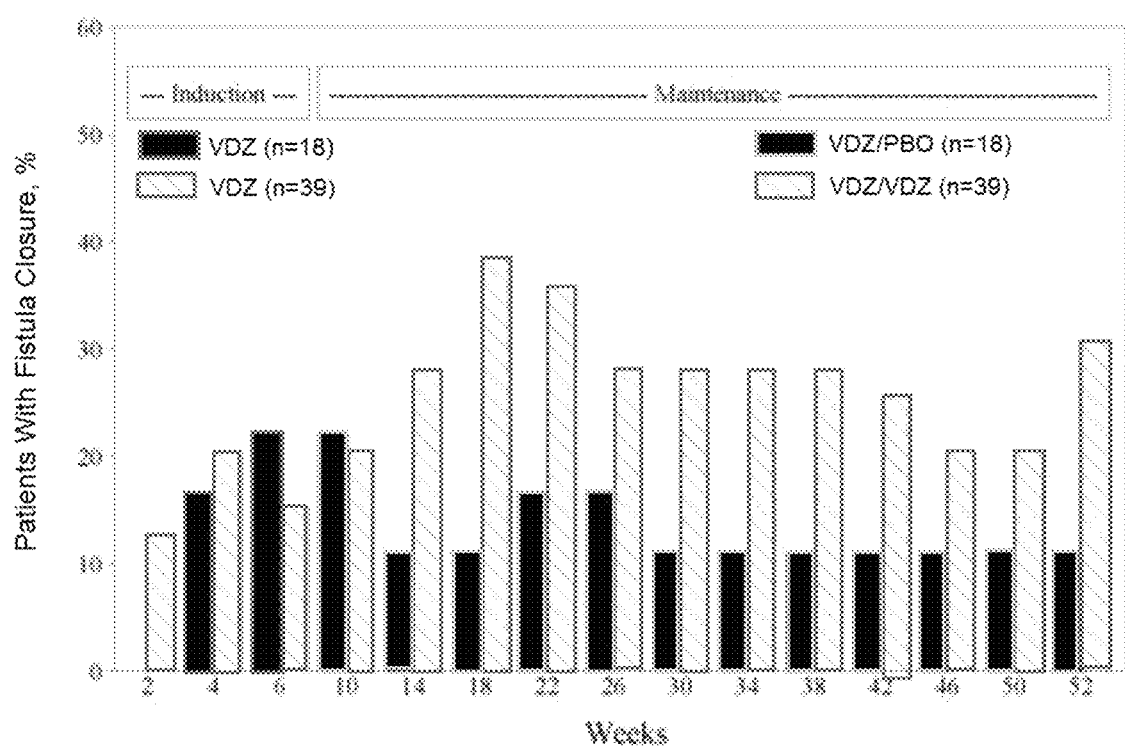
FIG. 1. Fistula closure by study visit (maintenance ITT population)

FIG. 2. Mean time to fistula closure in patients with ≥1 draining fistulae at week 0 (maintenance ITT population)
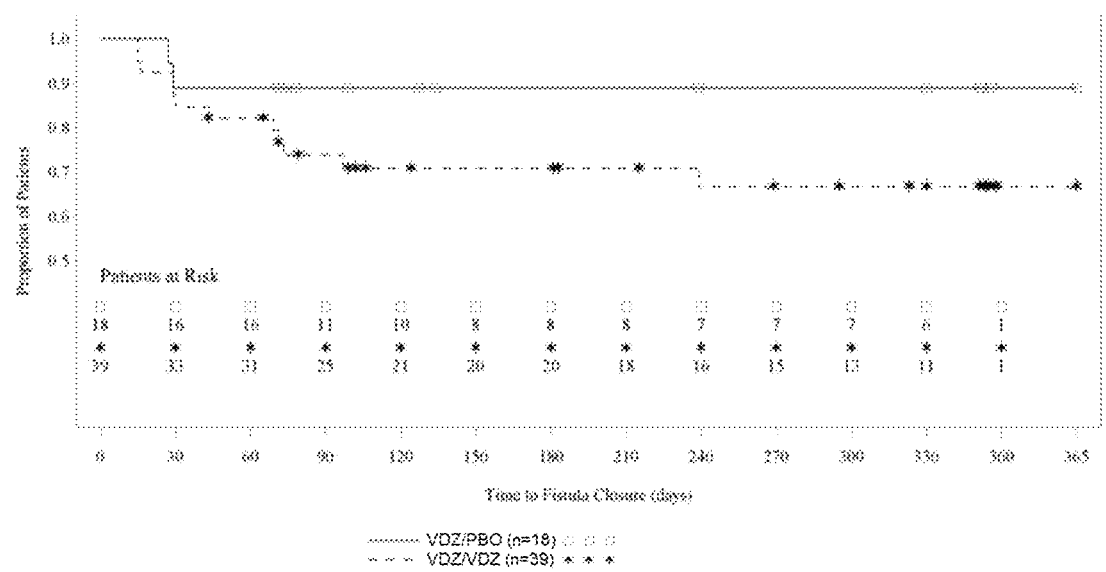

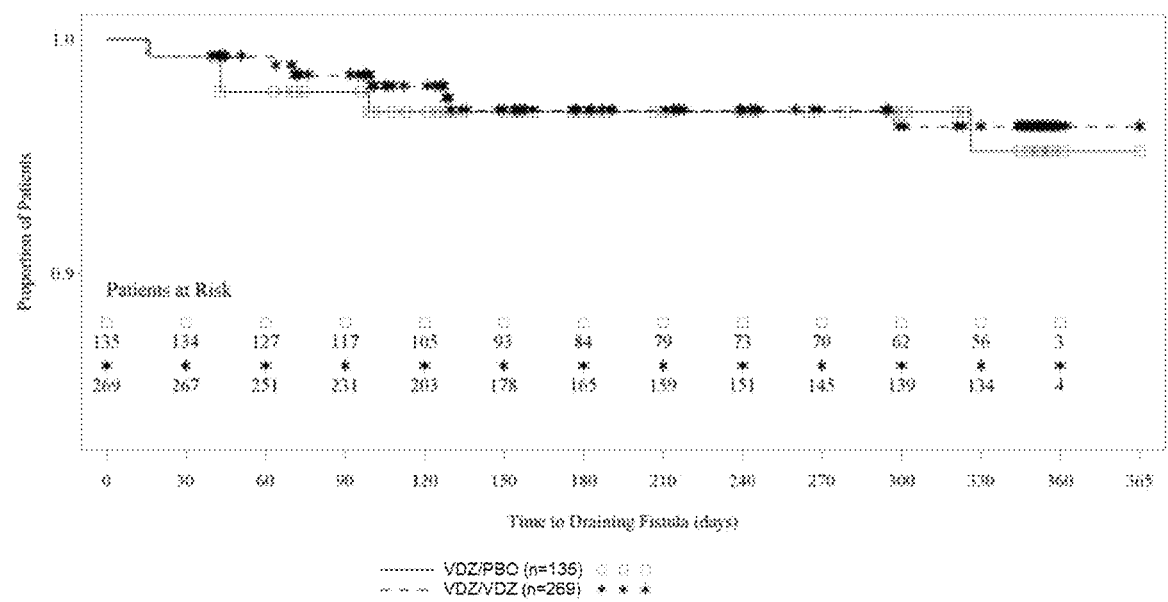
FIG.3 Mean time to open draining fistulae in patients without draining fistulae at week 0 (maintenance ITT population)

SEQUENCE LISTING

```
<160> NUMBER OF SEQ ID NOS: 11

<210> SEQ ID NO 1
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Gly Trp Ser Cys Ile Ile Leu Phe Leu Val Ala Thr Ala Thr Gly
 1               5                  10                  15
Val His Ser Gln Val Gln Leu Val Gln Ser Gly Ala Glu Val Lys Lys
                20                  25                  30
Pro Gly Ala Ser Val Lys Val Ser Cys Lys Gly Ser Gly Tyr Thr Phe
            35                  40                  45
Thr Ser Tyr Trp Met His Trp Val Arg Gln Ala Pro Gly Gln Arg Leu
        50                  55                  60
Glu Trp Ile Gly Glu Ile Asp Pro Ser Glu Ser Asn Thr Asn Tyr Asn
```

```
            65                  70                  75                  80
        Gln Lys Phe Lys Gly Arg Val Thr Leu Thr Val Asp Ile Ser Ala Ser
                        85                  90                  95

Thr Ala Tyr Met Glu Leu Ser Ser Leu Arg Ser Glu Asp Thr Ala Val
                       100                 105                 110

Tyr Tyr Cys Ala Arg Gly Gly Tyr Asp Gly Trp Asp Tyr Ala Ile Asp
                       115                 120                 125

Tyr Trp Gly Gln Gly Thr Leu Val Thr Val Ser Ser Ala Ser Thr Lys
                130                 135                 140

Gly Pro Ser Val Phe Pro Leu Ala Pro Ser Ser Lys Ser Thr Ser Gly
        145                 150                 155                 160

Gly Thr Ala Ala Leu Gly Cys Leu Val Lys Asp Tyr Phe Pro Glu Pro
                            165                 170                 175

Val Thr Val Ser Trp Asn Ser Gly Ala Leu Thr Ser Gly Val His Thr
                        180                 185                 190

Phe Pro Ala Val Leu Gln Ser Ser Gly Leu Tyr Ser Leu Ser Ser Val
                    195                 200                 205

Val Thr Val Pro Ser Ser Ser Leu Gly Thr Gln Thr Tyr Ile Cys Asn
                210                 215                 220

Val Asn His Lys Pro Ser Asn Thr Lys Val Asp Lys Lys Val Glu Pro
        225                 230                 235                 240

Lys Ser Cys Asp Lys Thr His Thr Cys Pro Pro Cys Pro Ala Pro Glu
                            245                 250                 255

Leu Ala Gly Ala Pro Ser Val Phe Leu Phe Pro Pro Lys Pro Lys Asp
                        260                 265                 270

Thr Leu Met Ile Ser Arg Thr Pro Glu Val Thr Cys Val Val Val Asp
                    275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
        305                 310                 315                 320

Ser Thr Tyr Arg Val Val Ser Val Leu Thr Val Leu His Gln Asp Trp
                            325                 330                 335

Leu Asn Gly Lys Glu Tyr Lys Cys Lys Val Ser Asn Lys Ala Leu Pro
                        340                 345                 350

Ala Pro Ile Glu Lys Thr Ile Ser Lys Ala Lys Gly Gln Pro Arg Glu
                    355                 360                 365

Pro Gln Val Tyr Thr Leu Pro Pro Ser Arg Asp Glu Leu Thr Lys Asn
                370                 375                 380

Gln Val Ser Leu Thr Cys Leu Val Lys Gly Phe Tyr Pro Ser Asp Ile
        385                 390                 395                 400

Ala Val Glu Trp Glu Ser Asn Gly Gln Pro Glu Asn Asn Tyr Lys Thr
                            405                 410                 415

Thr Pro Pro Val Leu Asp Ser Asp Gly Ser Phe Phe Leu Tyr Ser Lys
                        420                 425                 430

Leu Thr Val Asp Lys Ser Arg Trp Gln Gln Gly Asn Val Phe Ser Cys
                    435                 440                 445

Ser Val Met His Glu Ala Leu His Asn His Tyr Thr Gln Lys Ser Leu
                450                 455                 460

Ser Leu Ser Pro Gly Lys
        465                 470

<210> SEQ ID NO 2
```

<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Ala Lys Ser Tyr Gly Asn Thr Tyr Leu Ser Trp Tyr Leu Gln Lys Pro
    50                  55                  60

Gly Gln Ser Pro Gln Leu Leu Ile Tyr Gly Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Leu Gln Gly Thr His Gln Pro Tyr Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 3
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Gly
                 85                  90                  95

Thr His Gln Pro Tyr Thr Phe Gly Gln Gly Thr Lys Val Glu Ile Lys
            100                 105                 110

Arg Ala Asp Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Tyr Trp Met His
1               5
```

```
<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Ile Asp Pro Ser Glu Ser Asn Thr Asn Tyr Asn Gln Lys Phe Lys
1               5                   10                  15

Gly
```

```
<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Tyr Asp Gly Trp Asp Tyr Ala Ile Asp Tyr
1               5                   10
```

```
<210> SEQ ID NO 7
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ser Ser Gln Ser Leu Ala Lys Ser Tyr Gly Asn Thr Tyr Leu Ser
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Ile Ser Asn Arg Phe Ser
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Leu Gln Gly Thr His Gln Pro Tyr Thr
1               5

<210> SEQ ID NO 10
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Lys Val Glu Ile Lys
            100                 105                 110

<210> SEQ ID NO 11
<211> LENGTH: 119
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
            115
```

VEDOLIZUMAB FOR THE TREATMENT OF FISTULIZING CROHN'S DISEASE

RELATED APPLICATIONS

This application is a Continuation of U.S. patent application Ser. No. 15/529,308, filed on May 24, 2017, which is a United States National Phase under 35 U.S.C. § 371 of International Application No. PCT/US2015/062705, filed on Nov. 25, 2015, which claims the benefit of U.S. Provisional Application 62/084,815 filed on Nov. 26, 2014. The entire content of the foregoing application is hereby incorporated by reference.

BACKGROUND

Inflammatory bowel disease (IBD), such as ulcerative colitis and Crohn's disease (CD), for example, can be a debilitating and progressive disease involving inflammation of the gastrointestinal tract. IBD treatments have included anti-inflammatory drugs (such as, corticosteroids and sulfasalazine), immunosuppressive drugs (such as, 6-mercaptopurine, cyclosporine and azathioprine) and surgery (such as, colectomy). Podolsky, *New Engl. J. Med.*, 325:928-937 (1991) and Podolsky, *New Engl. J. Med.*, 325:1008-1016 (1991). As the disease progresses, treatment progresses into regimens that expose patients to progressive risk of side effects and loss of quality of life.

In contrast to the diffuse, superficial, continuous inflammation limited to the colon in ulcerative colitis, the inflammation of Crohn's disease is focal, may be transmural, and can involve any segment of the gastrointestinal (GI) tract from mouth to anus. The prevalence of CD is approximately 150/100,000 of the United States population and approximately 125/100,000 of population in Western Europe. The characteristic pathology involves a chronic inflammatory infiltrate consisting of neutrophils and macrophages. Hallmarks of CD include granulomatous inflammation and aphthous ulceration. CD is neither medically or surgically curable at the current time. A fistula is a chronic tract of granulation tissue between two epithelial lined surfaces. Fistulizing CD is a distinct disease subtype impacting CD patients. Patients with fistulizing CD experience symptoms of anal pain, purulent discharge and incontinence, which result in high morbidity and impaired quality of life.

Fistula(e) rarely heal spontaneously and usually require medical therapy or surgery. Although a range of medical and surgical options are available for CD, patients with fistula(e) have limited treatment options. There is no demonstrated role for aminosalicylates or corticosteroids in perianal CD. While antibiotics may contribute to healing, they are recommended as adjunctive therapy for fistula(e). Thiopurines may have a moderate effect in treating fistulizing Crohn's diseases, however the data are limited or mixed. Infliximab, a tumor necrosis factor (TNF) antagonist monoclonal antibody, has been shown to be effective in fistula(e) healing in two prospective randomized trials.

The management of perianal CD is challenging and often requires a comprehensive approach including both medical and surgical intervention, and thus there is a need to treat surgical therapy patients who may benefit from comprehensive therapy that includes administration of an of anti-α4β7 antibody, e.g., vedolizumab.

SUMMARY OF THE INVENTION

The invention relates to treatment of fistulizing Crohn's disease with an antagonist of the α4β7 integrin, such as an anti-α4β7 antibody (e.g., vedolizumab).

Thus, in a first aspect, the invention relates to a method for treating a human patient suffering from fistulizing Crohn's disease, wherein the method comprises the steps of administering to a patient suffering from fistulizing Crohn's disease, a humanized antibody having binding specificity for human α4β7 integrin, wherein the humanized antibody is administered to the patient according to the following dosing regimen: a) an initial dose of 300 mg of the humanized antibody as an intravenous infusion; b) followed by a second subsequent dose of 300 mg of the humanized antibody as an intravenous infusion at about two weeks after the initial dose; c) followed by a third subsequent dose of 300 mg of the humanized antibody as an intravenous infusion at about six weeks after the initial dose; d) followed by a fourth subsequent dose of 300 mg of the humanized antibody as an intravenous infusion at about ten weeks after the initial dose; e) followed by a fifth subsequent dose of 300 mg of the humanized antibody as an intravenous infusion at about 14 weeks after the initial dose; f) followed by a sixth and subsequent doses of 300 mg of the humanized antibody as an intravenous infusion every eight weeks after the fifth subsequent dose of the humanized antibody as needed; wherein the human patient has a seton that was surgically placed prior to administration of the antibody or antigen-binding fragment; wherein the dosing regimen induces fistula(e) healing; and further wherein the humanized antibody comprises an antigen binding region of nonhuman origin and at least a portion of an antibody of human origin, wherein the humanized antibody has binding specificity for the α4β7 complex, wherein the antigen-binding region comprises the CDRs: Light chain: CDR1 SEQ ID NO:7, CDR2 SEQ ID NO:8 and CDR3 SEQ ID NO:9; and Heavy chain: CDR1 SEQ ID NO:4, CDR2 SEQ ID NO:5 and CDR3 SEQ ID NO:6. In some embodiments, the fistula(e) is perianal fistula(e).

The fistula(e) healing may be measured by magnetic resonance imaging (MRI) assessment of fistula(e) healing at week 30. In some embodiments, at least 50% of draining fistulae are closed. In some embodiments, 100% of draining fistulae are closed. The patient may have had a lack of an adequate response with, loss response to, or was intolerant to treatment with at least one of an immunomodulator, a tumor necrosis factor-alpha antagonist or combinations thereof. In some embodiments, the patient may have had an inadequate response with, was intolerant to, or demonstrated dependence on corticosteroids.

In some embodiments, the Crohn's disease is moderately to severely active Crohn's disease. In some embodiments, the Crohn's disease is severely active.

The dosing regimen may result in a reduction, elimination or reduction and elimination of draining pads used by the patient.

In some embodiments, the humanized antibody is administered to the patient in about 30 minutes.

In some embodiments, the humanized antibody is reconstituted from a lyophilized formulation.

In some embodiments the humanized antibody is reconstituted to comprise a stable liquid formulation.

In some embodiments, the patient had a lack of an adequate response with or loss of response to a corticosteroid. In some embodiments, the immunomodulator is azathioprine, 6-mercaptopurine, or methotrexate.

Treatment may be measured by a PDAI score or a CDAI score of the patient. In some embodiments, the PDAI score of the patient is reduced by at least 3 points from baseline.

The humanized antibody may have a heavy chain variable region sequence of amino acids 20 to 140 of SEQ ID NO:1.

The humanized antibody may have a light chain variable region sequence of amino acids 20 to 131 of SEQ ID NO:2.

The humanized antibody may have a heavy chain comprising amino acids 20 to 470 of SEQ ID NO:1 and a light chain comprising amino acids 20 to 238 of SEQ ID NO:2. In some embodiments, the humanized antibody is vedolizumab.

In another aspect, the invention relates to a method for treating a human patient suffering from fistulizing Crohn's disease, wherein the method comprises the steps of administering to a patient suffering from fistulizing Crohn's disease, a humanized antibody having binding specificity for human α4β7 integrin, wherein the humanized antibody is administered to the patient according to the following dosing regimen: a) an initial dose of 300 mg of the humanized antibody as an intravenous infusion; b) followed by a second subsequent dose of 300 mg of the humanized antibody as an intravenous infusion at about two weeks after the initial dose; c) followed by a third subsequent dose of 300 mg of the humanized antibody as an intravenous infusion at about six weeks after the initial dose; d) followed by a fourth subsequent dose of 300 mg of the humanized antibodies an intravenous infusion at about 14 weeks after the initial dose; e) followed by a fifth and subsequent doses of 300 mg of the humanized antibody as an intravenous infusion every eight weeks after the fifth subsequent dose of the humanized antibody as needed; wherein the human patient has a seton that was surgically placed prior to administration of the antibody, wherein the dosing regimen induces fistula(e) healing; and further wherein the humanized antibody comprises an antigen binding region of nonhuman origin and at least a portion of an antibody of human origin, wherein the humanized antibody has binding specificity for the α4β7 complex, wherein the antigen-binding region comprises the CDRs: Light chain: CDR1 SEQ ID NO:7, CDR2 SEQ ID NO:8 and CDR3 SEQ ID NO:9; and Heavy chain: CDR1 SEQ ID NO:4, CDR2 SEQ ID NO:5 and CDR3 SEQ ID NO:6. In some embodiments, the fistula(e) are perianal fistula(e).

The fistula(e) healing may be measured by magnetic resonance imaging (MRI) assessment of fistula(e) healing at week 30. In some embodiments, at least 50% of draining fistulae are closed. In some embodiments, 100% of draining fistulae are closed.

BRIEF DESCRIPTION OF THE DRAWINGS

FIG. 1 is a graph, which shows the mean time to fistula closure in patients in the maintenance intent to treat (ITT) population with fistulizing disease. Patients in the placebo (PBO) group received vedolizumab (VDZ) at week 0 and week 2 in the 6-week induction phase. HR, hazard ratio (95% CI). All patients in the maintenance ITT population received induction treatment with VDZ. Patients in the VDZ/PBO maintenance group received VDZ in the 6-week induction phase and then PBO in the 46-week maintenance phase. Patients in the VDZ/VDZ maintenance group received VDZ during induction and either VDZ every 8 or every 4 weeks during maintenance.

FIG. 2 is a graph showing fistula closure by study visit in patients with one or greater draining fistula at week 0 (maintenance ITT population). Abbreviations: PBO, placebo; VDZ, vedolizumab. Patients in the VDZ/PBO group received VDZ in the 6-week induction phase and then PBO in the 46-week maintenance phase. Patients in the VDZ/VDZ group received VDZ during induction and either VDZ every 8 or every 4 weeks during maintenance.

FIG. 3 is a graph showing mean time to open draining fistulae in patients without draining fistulae at week 0 (maintenance ITT population). Abbreviations: PBO, placebo; VDZ, vedolizumab. Patients in the VDZ/PBO group received VDZ in the 6-week induction phase and then PBO in the 46-week maintenance phase. Patients in the VDZ/VDZ group received VDZ during induction and either VDZ every 8 or every 4 weeks during maintenance.

DETAILED DESCRIPTION

The invention relates to methods of treating Crohn's disease patients who have at least one fistula and have had a seton surgically implanted prior to medical treatment. A combination approach of surgical seton placement with an antagonist of the α4β7 integrin, such as an anti-α4β7 antibody (e.g., vedolizumab) is designed to provide maximum benefit to patients with one or more Crohn's fistula(e). In some embodiments, the treating comprises remission of Crohn's disease. In some embodiments, the fistula(e) is perianal. In other embodiments, the fistula(e) is enterocutaneous or abdominal. In some embodiments the fistula(e) is not rectovaginal.

One aspect of the invention comprises an α4β7 integrin antagonist (e.g., vedolizumab) for use in the treatment of a subject with fistulizing Crohn's disease, wherein the fistula (e) of the subject has received a surgically implanted seton.

Definitions

The term "pharmaceutical formulation" refers to a preparation that contains an α4β7 antagonist, such as an anti-α4β7 antibody, in such form as to permit the biological activity of the antibody to be effective, and which contains no additional components which are unacceptably toxic to a subject to which the formulation would be administered.

The cell surface molecule, "α4β7 integrin," or "α4β7," is a heterodimer of an $\alpha_4$ chain (CD49D, ITGA4) and a β7 chain (ITGB7). Each chain can form a heterodimer with an alternative integrin chain, to form $\alpha_4\beta_1$ or $\alpha_E\beta_7$. Human $\alpha_4$ and $\beta_7$ genes (GenBank (National Center for Biotechnology Information, Bethesda, MD) RefSeq Accession numbers NM_000885 and NM_000889, respectively) are expressed by B and T lymphocytes, particularly memory CD4+ lymphocytes. Typical of many integrins, α4β7 can exist in either a resting or activated state. Ligands for α4β7 include vascular cell adhesion molecule (VCAM), fibronectin and mucosal addressin (MAdCAM (e.g., MAdCAM-1)).

An "α4β7 antagonist" is a molecule which antagonizes, reduces or inhibits the function of α4β7 integrin. Such antagonist may antagonize the interaction of α4β7 integrin with one or more of its ligands. An α4β7 antagonist may bind either chain of the heterodimer or a complex requiring both chains of the α4β7 integrin, or it may bind a ligand, such as MAdCAM. An α4β7 antagonist may be an antibody which performs such binding function, such as an anti-α4β7-integrin antibody or "anti-α4β7 antibody". In some embodiments, an α4β7 antagonist, such as an anti-α4β7 antibody, has "binding specificity for the α4β7 complex" and binds to α4β7, but not to α4β1 or αEβ7.

The term "antibody" or "antibodies" herein is used in the broadest sense and specifically covers full length antibody, antibody peptide(s) or immunoglobulin(s), monoclonal antibodies, polyclonal antibodies, multispecific antibodies (e.g. bispecific antibodies) formed from at least two full length antibodies (e.g., each portion comprising the antigen binding region of an antibody to a different antigen or epitope), and individual antigen binding fragments of any of the foregoing, e.g., of an antibody or the antibody from which it is derived, including dAbs, scFv, Fab, F(ab')$_2$, Fab', including human, humanized and antibodies from non-human species and recombinant antigen binding forms such as monobodies and diabodies.

The term "human antibody" includes an antibody that possesses a sequence that is derived from a human germ-line immunoglobulin sequence, such as an antibody derived from transgenic mice having human immunoglobulin genes (e.g., XENOMOUSE genetically engineered mice (Abgenix, Fremont, CA), HUMAB-MOUSE®, KIRIN TC MOUSE™ transchromosome mice, KMMOUSE@(MEDAREX, Princeton, NJ)), human phage display libraries, human myeloma cells, or human B cells.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen binding sequences derived from a non-human primate (e.g. Old World Monkey, Ape etc) and human constant region sequences.

"Antigen binding fragments" of the humanized antibody prepared in the formulation of the invention comprise at least the variable regions of the heavy and/or light chains of an anti-α4β7 antibody. For example, an antigen binding fragment of vedolizumab comprises amino acid residues 20-131 of the humanized light chain sequence of SEQ ID NO:2. Examples of such antigen binding fragments include Fab fragments, Fab' fragments, scFv and F(ab')$_2$ fragments of a humanized antibody known in the art. Antigen binding fragments of the humanized antibody of the invention can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the CHI domain and hinge region of the heavy chain. In one aspect, antigen binding fragments inhibit binding of α4β7 integrin to one or more of its ligands (e.g. the mucosal addressin MAdCAM (e.g., MAdCAM-1), fibronectin).

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen binding sites and is still capable of cross-linking antigen.

"Fv" is an antibody fragment which consists of a dimer of one heavy chain variable domain and one light chain variable domain in non-covalent association.

The Fab fragment also contains the constant domain of the light chain and the first constant domain (CHI) of the heavy chain. Fab' fragments differ from Fab fragments by the addition of a few residues at the carboxy terminus of the heavy chain CH 1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the $V_H$ and $V_L$ domains of antibody, wherein these domains are present in a single polypeptide chain. In one aspect, the Fv polypeptide further comprises a polypeptide linker between the $V_H$ and $V_L$ domains which enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen binding sites. Diabodies are described more fully in, for example, EP 404,097; WO 93/11161; and Hollinger et al., Proc. Natl. Acad. Sci. USA, 90:6444-6448 (1993).

A "full length antibody" is one which comprises an antigen binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. In one aspect, the full length antibody has one or more effector functions.

An "amino acid sequence variant" antibody herein is an antibody with an amino acid sequence which differs from a main species antibody. Ordinarily, amino acid sequence variants will possess at least about 70%, at least about 80%, at least about 85%, at least about 90%, or at least about 95% homology with the main species antibody. The amino acid sequence variants possess substitutions, deletions, and/or additions at certain positions within or adjacent to the amino acid sequence of the main species antibody, but retain antigen binding activity. Variations in sequence of the constant regions of the antibody will have less effect on the antigen binding activity than variations in the variable regions. In the variable regions, amino acid sequence variants will be at least about 90% homologous, at least about 95% homologous, at least about 97% homologous, at least about 98% homologous, or at least about 99% homologous with the main species antibody.

"Homology" is defined as the percentage of residues in the amino acid sequence variant that are identical after aligning the sequences and introducing gaps, if necessary, to achieve the maximum percent homology. Methods and computer programs for the alignment are well known in the art.

A "therapeutic monoclonal antibody" is an antibody used for therapy of a human subject. Therapeutic monoclonal antibodies disclosed herein include anti-α4β7 antibodies.

A "glycosylation variant" antibody herein is an antibody with one or more carbohydrate moeities attached thereto which differ from one or more carbohydrate moieties attached to a main species antibody. Examples of glycosylation variants herein include antibody with a G1 or G2 oligosaccharide structure, instead of a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Antibody "effector functions" refer to those biological activities attributable to the Fc region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g. B cell receptor; BCR), and the like. To assess ADCC activity of a molecule of interest, an in vitro ADCC assay, such as that described in U.S. Pat. No. 5,500,362 or 5,821,337 may be performed.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of antibodies are well known.

The "light chains" of antibodies from any vertebrate species can be assigned to one of two clearly distinct types, called kappa (κ) and lambda (λ), based on the amino acid sequences of their constant domains.

The term "hypervariable region" when used herein refers to the amino acid residues of an antibody which are responsible for antigen binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human antibody are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human antibody and all or substantially all of the FRs are those of a human antibody sequence. The humanized antibody optionally also will comprise at least a portion of an antibody constant region (Fc), typically that of a human antibody. For further details, see Jones et al., *Nature* 321:522-525 (1986); Riechmann et al., *Nature* 332:323-329 (1988); and Presta, *Curr. Op. Struct. Biol.* 2:593-596 (1992).

An "affinity matured" antibody is one with one or more alterations in one or more hypervariable regions thereof which result an improvement in the affinity of the antibody for antigen, compared to a parent antibody which does not possess those alteration(s). In one aspect, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7): 3310-9 (1995); and Hawkins et al., *J. Mol. Biol.* 226:889-896 (1992).

An "isolated" antibody is one which has been identified and separated and/or recovered from a component of its natural environment. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disease as well as those in which the disease or its recurrence is to be prevented. Hence, the patient, e.g., human, to be treated herein may have been diagnosed as having the disease or may be predisposed or susceptible to the disease. The terms "patient" and "subject" are used interchangeably herein.

The antibody which is formulated is substantially pure and desirably substantially homogeneous (i.e. free from contaminating proteins etc). "Substantially pure" antibody means a composition comprising at least about 90% antibody by weight, based on total weight of the protein in the composition, at least about 95% or 97% by weight. "Substantially homogeneous" antibody means a composition comprising protein wherein at least about 99% by weight of protein is specific antibody, e.g., anti-$\alpha 4\beta 7$ antibody, based on total weight of the protein.

"Clinical remission" as used herein with reference to ulcerative colitis subjects refers to a complete Mayo score of 2 or less points and no individual subscore greater than 1 point. Crohn's disease "clinical remission" refers to a CDAI score of 150 points or less.

A "clinical response" as used herein with reference to Crohn's disease subjects refers to a 70 point or greater decrease in CDAI score from baseline (week 0).

As used herein, "treatment failure" refers to disease worsening, a need for rescue medications or surgical intervention for treatment of Crohn's disease. A rescue medication is any new medication or any increase in dose of a baseline medication required to treat new or unresolved Crohn's disease symptoms (other than antidiarrheals for control of chronic diarrhea).

An anti-$\alpha 4\beta 7$ antibody, vedolizumab, a humanized monoclonal antibody that has binding specificity for the $\alpha 4\beta 7$ integrin, is indicated for the treatment of patients with moderately to severely active ulcerative colitis (UC) and Crohn's disease (CD). Vedolizumab has a novel gut-selective mechanism of action that differs from that of other currently marketed biologic agents for the treatment for inflammatory bowel disease (IBD), including natalizumab and tumor necrosis factor-$\alpha$ (TNF-$\alpha$) antagonists. By binding to cell surface-expressed $\alpha_4\beta_7$, vedolizumab is an $\alpha 4\beta 7$ antagonist and blocks the interaction of a subset of memory gut-homing T lymphocytes with mucosal addressin cell adhesion molecule-1 (MAdCAM-1) expressed on endothelial cells. Consequently, migration of these cells into inflamed intestinal tissue is inhibited.

The pharmacokinetics of other therapeutic monoclonal antibodies used for the treatment of CD have been previously reported. Several factors are associated with accelerated clearance of these antibodies including the presence of anti-drug antibodies, sex, body size, concomitant immunosuppressant use, disease type, albumin concentration, and degree of systemic inflammation. Furthermore, a consistent relationship between efficacy and exposure, in distinction to drug dose, has been observed for many of these agents, such that higher trough drug concentrations are associated with greater efficacy. Differences in drug clearance may be an important explanation for this observation. Therefore, a better understanding of the determinants of clearance for therapeutic antibodies may result in optimization of drug regimens.

In previous studies, single-dose pharmacokinetics, pharmacodynamics (aj37 receptor saturation), safety, and tolerability of vedolizumab were investigated over a dose range of 0.2 to 10 mg/kg in healthy volunteers (intravenous [IV] infusion) (unpublished data). After reaching peak concentrations, vedolizumab serum concentrations fell in a generally biexponential fashion until concentrations reached approximately 1 to 10 ng/mL. Thereafter, concentrations appeared to fall in a nonlinear fashion. The multiple-dose pharmacokinetics and pharmacodynamics of vedolizumab have been investigated following IV infusions of 0.5 and 2 mg/kg in patients with CD and infusion of 2, 6, and 10 mg/kg in patients with UC. Vedolizumab pharmacokinetics was generally linear following an IV infusion over the dose range of 2 to 10 mg/kg in patients with UC. After multiple-dose administration, rapid and near complete $\alpha_4\beta_7$ receptor saturation was achieved following the initial dose of vedolizumab.

The efficacy and safety of vedolizumab induction and maintenance therapy were demonstrated in patients with CD in the GEMINI 2 (ClinicalTrials.gov number, NCT00783692) and GEMINI 3 (ClinicalTrials.gov number, NCT01224171) trials. The exposure-response (efficacy) relationships of vedolizumab in patients with CD for induction and maintenance therapy have been presented elsewhere.

As used herein, fistula(e) refers to one fistula and/or two or more fistulae.

Treatment of Fistulizing Crohn's Disease with Anti-$\alpha 4\beta 7$ Antibodies

In one aspect, the invention relates to a method of treating fistulizing Crohn's disease in a human patient comprising administering to the patient an anti-$\alpha 4\beta 7$ antibody described herein in an amount effective to treat a fistula(e), e.g., a draining perianal fistula(e) and/or a fistula(e) in another location e.g., an abdominal or an enterocutaneous fistula(e). The human patient may be an adult (e.g., 18 years or older), an adolescent, or a child. A pharmaceutical composition comprising an anti-$\alpha 4\beta 7$ antibody can be used as described herein for treating fistulizing Crohn's disease in a subject suffering therefrom. The fistula(e) may have been open for 2 weeks, 4 weeks, 6 weeks, 2 months, 3 months, 4 months, 6 months, 3 to 6 months, 2 to 4 months or 3 to 7 months prior to treatment with an $\alpha 4\beta 7$ antagonist. Prior to treatment with an $\alpha 4\beta 7$ antagonist, e.g., an anti-$\alpha 4\beta 7$ antibody, such as vedolizumab, the human patient shall have had a seton surgically implanted at the site of the fistula(e). The seton may have been surgically placed about 1 week, about 2 weeks, about 3 weeks, about 4 weeks, about 5 weeks, or about 6 weeks prior to administration of an anti-$\alpha 4\beta 7$ antibody. The seton may be a noncutting seton. The seton surgically placed prior to administration of an anti-$\alpha 4\beta 7$ antibody may be removed during treatment, for example, the seton may be removed at or after week 10, at or after week 14, at or after week 22 or between weeks 22 and 30. The seton may be removed any time after significant reduction in fistula(e) drainage is observed.

A seton placement is a surgical procedure used to aid in the healing of fistula(e). The procedure involves running a surgical-grade cord through the fistula tract so that the cord creates a loop that joins up outside the fistula. The cord provides a path which allows the fistula to drain continuously while it is healing, rather than allowing the exterior of the wound to close over. Keeping the fistula tract open can help keep from trapping pus or other infectious material in the wound. Setons may be tied tightly or loosely and with different materials, depending on the anatomical location of the fistula(e) and what may be medically required. A seton may be tied loosely as a palliative measure to avoid septic and painful exacerbations, or as temporary measure before surgical excision as in fistulotomy or fistulectomy. In some types of fistula(e), a seton may be tied with more tension and tightened periodically. In this case, the seton loop will slowly cut through tissue inside the loop while scarring behind the loop, essentially "pulling out" the fistula without surgery. The patient may have had a lack of an adequate response with, loss of response to, or was intolerant to treatment with an immunomodulator, a TNF-α antagonist, or combinations thereof. The patient may have had an inadequate response with, lost response to, or been intolerant to either conventional therapy or a tumor necrosis factor-alpha (TNF-α) antagonist for their underlying CD. The patient may have previously received treatment with at least one corticosteroid (e.g., prednisone) for the fistulizing Crohn's disease. The patient may have had an inadequate response with, were intolerant to, or demonstrated dependence on corticosteroids. An inadequate response to corticosteroids refers to signs and symptoms of persistently active disease despite a history of at least one 4-week induction regimen that included a dose equivalent to prednisone 30 mg daily orally for 2 weeks or intravenously for 1 week.

A loss of response to corticosteroids refers to two failed attempts to taper corticosteroids to below a dose equivalent to prednisone 10 mg daily orally. Intolerance of corticosteroids includes a history of Cushing's syndrome, osteopenia/osteoporosis, hyperglycemia, insomnia and/or infection.

An immunomodulator may be, for example, oral azathioprine, 6-mercaptopurine, or methotrexate. An inadequate response to an immunomodulator refers to signs and symptoms of persistently active disease despite a history of at least one 8 week regimen or oral azathioprine ($\geq 1.5$ mg/kg), 6-mercaptopurine ($\geq 0.75$ mg/kg), or methotrexate ($\geq 12.5$ mg/week). Intolerance of an immunomodulator includes, but is not limited to, nausea/vomiting, abdominal pain, pancreatitis, liver function test (LFT) abnormalities, lymphopenia, thiopurine methyltransferase (TPMT) genetic mutation and/or infection.

In one aspect, the patient may have had a lack of an adequate response with, loss of response to, or was intolerant to treatment by a TNF-α antagonist. A TNF-α antagonist is, for example, an agent that inhibits the biological activity of TNF-α, and preferably binds TNF-α, such as a monoclonal antibody, e.g., REMICADE (infliximab), HUMIRA (adalimumab), CIMZIA (certolizumab pegol), SIMPONI (golimumab) or a circulating receptor fusion protein such as ENBREL (etanercept). An inadequate response to a TNF-α antagonist refers to signs and symptoms of persistently active disease despite a history of at least one 4 week induction regimen of infliximab 5 mg/kg IV, 2 doses at least 2 weeks apart; one 80 mg subcutaneous dose of adalimumab, followed by one 40 mg dose at least two weeks apart; or 400 mg subcutaneously of certolizumab pegol, 2 doses at least 2 weeks apart. A loss of response to a TNF-α antagonist refers to recurrence of symptoms during maintenance dosing following prior clinical benefit. Intolerance of a TNF-α antagonist includes, but is not limited to infusion related reaction, demyelination, congestive heart failure, and/or infection.

Treatment may result in fistula healing in patients suffering from moderately to severely active Crohn's disease. As used herein, "moderately to severely active Crohn's disease" refers to Crohn's disease with a CDAI score ranging from 220 to 400. In some embodiments, treatment may result in fistula healing of patients with a CDAI score of less than 330, 220 to 350, or 220 to 330 prior to treatment. In some embodiments, treatment may result in fistula healing in patients suffering from severely active Crohn's disease. In some embodiments, treatment may result in fistula healing of patients with a CDAI score of more than 330, 330 to 400, 350 to 450 or 330 to 450 prior to treatment. In some embodiments, treatment may result in fistula healing of patients with a CDAI score of more than 350, more than 400, more than 425, or in the range of 375 to 500 or 400 to 600. Treatment may prevent the need for surgery, e.g., fistulectomy or fistulotomy, to remove the fistula or the fistula-containing tissue or other surgery for Crohn's disease, e.g., strictureplasty, resection, colectomy or proctocolectomy. In reference to Crohn's disease, "fistula healing" results in closure or elimination of fistula(e). In some embodiments, healed fistula(e) are closed and no longer draining despite gentle finger compression. Fistula healing may be evaluated by magnetic resonance imaging (MRI), for example a pelvic MRI. MRI may be used to classify the patient's fistula(e) as per Parks' criteria for classification as simple or complex fistula(e) (or intersphincteric, transsphincteric, suprasphincteric, or extrasphincteric), for scoring using the Van Assche MRI score, and/or to measure fistula(e) healing by reduction in T2 hyperintensity from baseline. MRI may be used to assess change in inflammatory process from baseline on post-contrast enhanced T1-weighted images. Van Assche is a MRI-based scoring method for assessment of disease severity in patients with perianal fistulizing CD. The scoring method comprises six components (number of fistula tracks, location, extension, hyperintensity on T2-weighted images, collections, rectal wall involvement), summed to a total score of 0 to 24. This objective scoring method may be used to assess response to therapy. T1- and T2-weighted images of the perianal region (pelvic MRI) may be reviewed to classify the fistula(e) and assess the full extent of the perianal disease. Local inflammatory activity may be assessed on T2-weighted images. Active fistula(e) and abscesses with active inflammatory process are visible on T2 images as hyperintense lesions due to their fluid contents, while scar tissue appears hypointense. Relative mean T2 signal intensity changes may be assessed by comparing normalized T2 signal intensity values of inflamed perianal regions including fistula tracts to T2 signal intensity of healthy tissue (e.g., muscle or fat). Additionally, post Gadolinium contrast enhanced T1-weighted imaging may be performed. Contrast-enhanced T1-weighted images may be compared to baseline images to assess response to therapy. In some embodiments, treatment may result in fistula healing as measured by reduction in T2 hyperintensity from baseline and assess change in inflammatory process from baseline on post-contrast enhanced T1-weighted images.

Treatment may result in improved clinical disease activity as assessed by Perianal Disease Activity Index (PDAI) and/or Crohn's Disease Activity Index (CDAI) from the time of starting treatment (Day 1) as compared to weeks 2, 6, 10, 14, 22, and 30. The PDAI comprises five categories: discharge, pain, restriction of sexual activity, type of fistulizing disease, e.g., perianal disease and degree of induration. Each category is graded on a five-point scale, ranging from no symptoms (score 0) to severe symptoms (score 4). PDAI scores may range from 0 to 20, with higher scores indicating more severe disease. In some embodiments, the PDAI score after treatment or after 6 weeks, 10 weeks, 14 weeks or 22 weeks of treatment may be reduced by at least 3 points from baseline, by at least 6 points from baseline, by at least 8 points from baseline, by at least 10 points from baseline or to a range of 2 to 10 points, 3 to 12 points, 1 to 8 points, 0 to 6 points or 0 to 4 points. The CDAI score after treatment or after 6 weeks, 10 weeks, 14 weeks or 22 weeks of treatment may be less than 200, less than 190, less than 180, less than 170, less than 160, less than 150 points, or in a range of 100 to 200 points, 175 to 125 points, 175 to 75 points, or 150 to 0 points. A CDAI score below 150 points is regarded as remission.

In some aspects, fistula healing is seen after about 4 weeks, about 6 weeks, about 8 weeks, 10 weeks, about 12 weeks, about 14 weeks, about 15 weeks, about 20 weeks, about 22 weeks, about 30 weeks, after beginning treatment. In some embodiments, the first fistula closes by about 3 weeks, about 4 weeks, about 5 weeks, about 6 weeks or about 8 weeks after beginning treatment or within 1 to 3 weeks, within 2 to 4 weeks, 3 to 5 weeks or 3 to 7 weeks of the initial dose of the α4β7 antagonist. Fistula healing may be partial fistula healing, in which about 30%, about 35%, 0%, a 40%, about 45%, about 50%, about 55%, about 60%, about 65%, about 70%, about 75%, about 80%, about 85%, about 90%, or about 95% of the patient's fistula(e) have healed. In some embodiments, partial fistula healing occurs by about 4 weeks, about 5 weeks, about 6 weeks, about 8 weeks, about 10 weeks, about 12 weeks or by about 14 weeks after beginning treatment or within 3 to 5 weeks, 3 to 7 weeks, 6 to 22 weeks, 8 to 14 weeks or 10 to 22 weeks of the initial dose of the α4β7 antagonist. In some aspects, 100% of the fistula(e) present at the beginning of treatment have healed. Reduction in the number of draining fistula(e) may be observed on the basis of a physician's physical evaluation of the patient using gentle finger compression to assess whether drainage occurred. In some embodiments, the number of fistula(e) is reduced by 1. In other embodiments, the number of fistula(e) is reduced by 2, 3 or 4. This reduction may be between weeks 4 to 8, weeks 6 to 10, weeks 8 to 12 or weeks 6 to 14 of treatment. 100% fistula(e) closure is defined herein as where all fistula(e) are no longer draining despite gentle finger compression. In some embodiments, 100% of fistula(e) are closed by 6 to 14 weeks, 8 to 16 weeks, 10 to 20 weeks, 14 to 22 weeks, 20 to 30 weeks or 12 to 30 weeks after the initial dose of the α4β7 antagonist. In an embodiment, 100% of fistula(e) are closed by 30 weeks after the initial dose of the α4β7 antagonist. In some embodiments, the α4β7 antagonist is vedolizumab. In some embodiments, α4β7 antagonist treatment results in 100% of fistula(e) closure in 20% to 40% of patients, 30% to 50% of patients, 25% to 60% of patients, 35% to 70% of patients, at least 50% of patients, at least 65% of patients, at least 75% of patients. In some embodiments, seton placement prior to α4β7 antagonist treatment plus 2 to 6 doses of α4β7 antagonist treatment results in 100% of fistula closure and seton removal by week 30 of treatment.

In some aspects, treatment may result in a reduced number of pads used for fistula(e) drainage. The number of pads used daily by the patient for fistula(e) drainage may be reduced by about 10%, about 20%, about 30%, about 40%, about 50%, about 60%, about 70%, about 80% or about 90%. The patient may stop needing pads for fistula(e) drainage after treatment with an anti-α4β7 antibody (100% reduction). This reduction may occur by 3 weeks, by 4 weeks, by 6 weeks, by 8 weeks, by 10 weeks, by 12 weeks within 3 to 6 weeks, within 4 to 8 weeks, within 6 to 10 weeks, within 8 to 14 weeks, after beginning treatment with the α4β7 antagonist.

In some aspects, treatment with the α4β7 antagonist after fistula(e) closure, e.g., after 4 to 8 doses of α4β7 antagonist or continued treatment with the antagonist, maintains fistula(e) closure or prevents development of new fistula(e) or draining fistula(e). In some embodiments, maintenance of fistula(e) closure has at least a 3 month duration. For example, maintenance of fistula(e) closure is 3 to 6 months, 4 to 9 months, 6 to 12 months, 9 to 16 months, 12 to 18 months, 16 to 24 months or more than 30 months. In some embodiments, the duration of maintenance of fistula(e) closure is not less than 6 months, not less than 9 months, not less than 12 months, not less than 16 months, not less than 24 months, not less than 30 months. In some embodiments, the maintenance of fistula(e) closure comprises continued treatment with the α4β7 antagonist. In an embodiment, the maintenance of fistula(e) closure comprises treatment with an anti-α4β7 antibody. In some embodiments the anti-α4β7 antibody administered during the maintenance of fistula(e) closure is vedolizumab. In some embodiments, vedolizumab is for use in maintaining fistula(e) closure. In such embodiments, vedolizumab may be administered once every 2 weeks, once every 4 weeks, once every 8 weeks, once every 10 weeks or once every 12 weeks.

Treatment may also result in a reduction, elimination, or reduction and elimination of corticosteroid use by the patient.

A formulation of the α4β7 antagonist, such as an anti-α4β7 antibody is administered in an effective amount which inhibits binding of α4β7 integrin to a ligand thereof. For therapy, an effective amount will be sufficient to achieve the desired therapeutic (including prophylactic) effect (such as an amount sufficient to reduce and/or eliminate the number of draining fistula(e)). An effective amount of an anti-α4β7 antibody, e.g., an effective titer sufficient to maintain saturation, e.g., neutralization, of α4β7 integrin, can induce fistula(e) healing, clinical response or remission in Crohn's disease. A formulation of the invention may be administered in a unit dose or multiple doses. The dosage can be determined by methods known in the art and can be dependent, for example, upon the individual's age, sensitivity, tolerance and overall well-being. Examples of modes of administration include topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for antibodies can be from about 0.1 mg/kg body weight to about 10.0 mg/kg body weight per treatment, for example about 2 mg/kg to about 7 mg/kg, about 3 mg/kg to about 6 mg/kg, or about 3.5 to about 5 mg/kg. In particular embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. In some embodiments, vedolizumab is administered at a dose of 50 mg, 100 mg, 300 mg, 500 mg or 600 mg. In some embodiments, vedolizumab is administered at a dose of 108 mg, 216 mg, 160 mg, 165 mg, 155 to 180 mg, 170 mg or 180 mg.

In the case of an antibody formulation which is stored as a lyophilized solid, the antibody is reconstituted in a solution such as water for injection prior to administration. If prepared for infusion, the final dosage form, e.g., after dilution of the reconstituted antibody (e.g., in a saline, Ringer's or 5% dextrose infusion system) of the anti-α4β7 antibody can be about 0.5 mg/ml to about 5 mg/ml for administration. The final dosage form may be at a concentration of between about 1.0 mg/ml to about 1.4 mg/ml, about 1.0 mg/ml to about 1.3 mg/ml, about 1.0 mg/ml to about 1.2 mg/ml, about 1.0 to about 1.1 mg/ml, about 1.1 mg/ml to about 1.4 mg/ml, about 1.1 mg/ml to about 1.3 mg/ml, about 1.1 mg/ml to about 1.2 mg/ml, about 1.2 mg/ml to about 1.4 mg/ml, about 1.2 mg/ml to about 1.3 mg/ml, or about 1.3 mg/ml to about 1.4 mg/ml. The final dosage form may be at a concentration of about 0.6 mg/ml, 0.8 mg/ml, 1.0 mg/ml, 1.1 mg/ml, about 1.2 mg/ml, about 1.3 mg/ml, about 1.4 mg/ml, about 1.5 mg/ml, about 1.6 mg/ml, about 1.8 mg/ml or about 2.0 mg/ml. In one embodiment, the total dose is 180 mg. In another embodiment, the total dose is 300 mg. A 300 mg anti-α4β7 antibody dose may be diluted into a 250 ml saline, Ringer's or 5% dextrose solution for administration.

In some aspects, the dosing regimen has two phases, an induction phase and a maintenance phase. In the induction phase, the antibody is administered in a way that quickly provides an effective amount of the antibody or antigen binding fragment thereof suitable for certain purposes, such as inducing immune tolerance to the antibody or for inducing a clinical response and ameliorating Crohn's disease symptoms. A patient may be administered an induction phase treatment when first being treated by an anti-α4β7 antibody, when being treated after a long absence from therapy, e.g., more than three months, more than four months, more than six months, more than nine months, more than one year, more than eighteen months or more than two years since anti-α4β7 antibody therapy or during maintenance phase of anti-α4β7 antibody therapy if there has been a return of fistulizing Crohn's disease symptoms, e.g., a relapse from remission of disease. In some embodiments, the induction phase regimen results in a higher mean trough serum concentration, e.g., the concentration just before the next dose, than the mean steady state trough serum concentration maintained during the maintenance regimen.

In the maintenance phase, the antibody is administered in a way that continues the response achieved by induction therapy with a stable level of antibody. A maintenance regimen can prevent return of symptoms or relapse of fistulizing Crohn's disease. A maintenance regimen can provide convenience to the patient, e.g., by a simple dosing regimen or require infrequent trips for treatment. In some embodiments, the maintenance regimen can include administration of the anti-α4β7 antibody, e.g., in a formulation described herein, by a strategy selected from the group consisting of low dose, infrequent administration, self-administration and a combination any of the foregoing.

In one embodiment, e.g., during an induction phase of therapy, the dosing regimen provides an effective amount of an anti-α4β7 antibody in a formulation described herein for inducing remission of an inflammatory bowel disease in a human patient. In some embodiments, the effective amount of the anti-α4β7 antibody is sufficient to achieve about 5 µg/ml to about 60 µg/ml, about 15 µg/ml to about 45 µg/ml, about 20 µg/ml to about 30 µg/ml, or about 25 µg/ml to about 35 µg/ml mean trough serum concentration of the anti-α4β7 antibody by the end of the induction phase. The duration of induction phase can be about four weeks, about five weeks, about six weeks, about seven weeks, or about eight weeks of treatment. In some embodiments, the induction regimen can utilize a strategy selected from the group consisting of high dose, frequent administration, and a combination of high dose and frequent administration of the anti-α4β7 antibody, e.g., in a formulation described herein. Induction dosing can be once, or a plurality of more than one dose, e.g., at least two doses. During induction phase, a dose can be administered once per day, every other day, twice per week, once per week, once every ten days, once every two weeks or once every three weeks. In some embodiments, the induction doses are administered within the first two weeks of therapy with the anti-α4β7 antibody. In one embodiment, induction dosing can be once at initiation of treatment (day 0) and once at about two weeks after initiation of treatment. In another embodiment, the induction phase duration is six weeks. In another embodiment, the induction phase duration is six weeks and a plurality of induction doses are administered during the first two weeks. In another embodiment, the induction phase duration is ten weeks.

In some embodiments, e.g., when initiating treatment of a patient with severe Crohn's disease (e.g., in patients who have failed anti-TNFα therapy), the induction phase needs to have a longer duration than for patients with mild or moderate disease. In some embodiments, the induction phase for a patient with a severe disease can have a duration of at least 6 weeks, at least 8 weeks, at least 10 weeks, at least 12 weeks or at least 14 weeks. In one embodiment, an induction dosing regimen for a patient with a severe disease can include a dose at week 0 (initiation of treatment), a dose at week 2 and a dose at week 6. In another embodiment, an induction dosing regimen for a patient with a severe disease can comprise a dose at week 0 (initiation of treatment), a dose at week 2, a dose at week 6 and a dose at week 10.

In one embodiment, e.g., during a maintenance phase of therapy, the dosing regimen maintains a mean steady state trough serum concentration, e.g., the plateau concentration just before the next dose, of about 5 to about 40 µg/mL, about 5 to about 25 µg/mL, about 7 to about 20 µg/mL, about 5 to about 10 µg/mL, about 10 to about 40 µg/mL, about 10 to about 20 µg/mL, about 15 to about 25 µg/mL or about 9 to about 13 µg/mL of anti-α4β7 antibody. In another embodiment, the dosing regimen e.g., during a maintenance phase of therapy, maintains a mean steady state trough serum concentration of about 15 to about 40 µg/mL, about 20 to about 30 µg/mL, about 20 to about 55 µg/mL, about 30 to about 45 µg/mL, about 45 to about 55 µg/mL or about 35 to about 40 µg/mL of anti-α4β7 antibody.

The dose can be administered once per week, once every 2 weeks, once every 3 weeks, once every 4 weeks, once every 6 weeks, once every 8 weeks or once every 10 weeks. A higher or more frequent dose, e.g., once per week, once every 2 weeks, once every 3 weeks or once every 4 weeks can be useful for inducing remission of active disease or for treating a new patient, e.g., for inducing tolerance to the anti-α4β7 antibody. A less frequent dose, e.g., once every 4 weeks, once every 5 weeks, once every 6 weeks, once every 8 weeks or once every 10 weeks, can be useful for preventative therapy, e.g., to maintain remission of a patient with chronic disease. In one aspect, the treatment regimen is treatment at day 0, about week 2, about week 6, about week 10, and every 4 or 8 weeks thereafter. In one embodiment, the maintenance regimen includes a dose every 8 weeks. In an embodiment, wherein a patient on a one dose every eight weeks maintenance regimen experiences a return of one or more disease symptoms, e.g., has a relapse, the dosing frequency can be increased, e.g., to once every 4 weeks.

The dose can be administered to the patient in about 20 minutes, about 25 minutes, about 30 minutes, about 35 minutes, or about 40 minutes.

The dosing regimen can be optimized to induce fistula(e) healing, clinical response and clinical remission in the Crohn's disease of the patient. In some embodiments, the dosing regimen does not alter the ratio of CD4 to CD8 in cerebrospinal fluid of patients receiving treatment.

In some aspects, a durable clinical remission, for example, a clinical remission which is sustained through at least two, at least three, at least four visits with a caretaking physician within a six month or one year period after beginning treatment may be achieved with an optimized dosing regimen.

In some aspects, a durable clinical response, for example, a clinical response which is sustained for at least 6 months, at least 9 months, at least a year, after the start of treatment, may be achieved with an optimized dosing regimen.

In one embodiment, the dosing regimen comprises an initial dose of 300 mg, a second subsequent dose of 300 mg about two weeks after the initial dose, a third subsequent dose of 300 mg at about six weeks after the initial dose, a fourth subsequent dose of 300 mg at about 10 weeks after the initial dose, a fifth subsequent dose of 300 mg at about 14 weeks after the initial dose, and subsequent doses of 300 mg every four weeks or every eight weeks after the fifth subsequent dose.

The vedolizumab may be administered once per day, per week, per month, or per year. In some embodiments, vedolizumab is administered one or more times, and then at least one month, at least six months, or at least one year later, vedolizumab is again administered one or more times. In some embodiments, 300 mg vedolizumab may be administered by intravenous infusion at zero, two, and six weeks, and then at four weeks intervals or eight week intervals thereafter. In some embodiments, 300 mg vedolizumab may be administered by intravenous infusion at zero, two, and six weeks, and then at two, three or four weeks intervals, 108 mg of vedolizumab may be administered subcutaneously.

In some embodiments, the method of treatment, dose or dosing regimen reduces the likelihood that a patient will develop a human-anti-human antibody (HAHA) response to the anti-α4β7 antibody. The development of HAHA, e.g., as measured by antibodies reactive to the anti-α4β7 antibody, can increase the clearance of the anti-α4β7 antibody, e.g., reduce the serum concentration of the anti-α4β7 antibody, e.g., lowering the number of anti-α4β7 antibody bound to α4β7 integrin, thus making the treatment less effective. In some embodiments, to prevent HAHA, the patient can be treated with an induction regimen followed by a maintenance regimen. In some embodiments, there is no break between the induction regimen and the maintenance regimen. In some embodiments, the induction regimen comprises administering a plurality of doses of anti-α4β7 antibody to the patient. To prevent HAHA, the patient can be treated with a high initial dose, e.g., at least 1.5 mg/kg, at least 2 mg/kg, at least 2.5 mg/kg, at least 3 mg/kg, at least 5 mg/kg, at least 8 mg/kg, at least 10 mg/kg or about 2 to about 6 mg/kg, or frequent initial administrations, e.g., about once per week, about once every two weeks or about once every three weeks, of the standard dose when beginning therapy with an anti-α4β7 antibody. In some embodiments, the method of treatment maintains at least 30%, at least 40%, at least 50%, at least 60%, at least 70%, at least 80%, at least 90% or at least 95% of patients as HAHA-negative. In other embodiments, the method of treatment maintains patients as HAHA-negative for at least 6 weeks, at least 10 weeks at least 15 weeks, at least six months, at least 1 year, at least 2 years, or for the duration of therapy. In some embodiments, the patients, or at least 30%, at least 40%, at least 50% or at least 60% of patients who develop HAHA maintain a low titer, e.g., ≤125, of anti-α4β7 antibody. In an embodiment, the method of treatment maintains at least 70% of patients as HAHA-negative for at least 12 weeks after beginning therapy with an anti-α4β7 antibody.

The formulation of an anti-α4β7 antibody may be administered to an individual (e.g., a human) alone or in conjunction with another agent. A formulation of the invention can be administered before, along with or subsequent to administration of the additional agent. In one embodiment, more than one formulation which inhibits the binding of α4β7 integrin to its ligands is administered. In such an embodiment, an agent, e.g., a monoclonal antibody, such as an anti-MAdCAM (e.g., anti-MAdCAM-1) or an anti-VCAM-1 monoclonal antibody can be administered. In another embodiment, the additional agent inhibits the binding of leukocytes to an endothelial ligand in a pathway different from the α4β7 pathway. Such an agent can inhibit the binding, e.g. of chemokine (C—C motif) receptor 9 (CCR9)-expressing lymphocytes to thymus expressed chemokine (TECK or CCL25) or an agent which prevents the binding of LFA-1 to intercellular adhesion molecule (ICAM). For example, an anti-TECK or anti-CCR9 antibody or a small molecule CCR9 inhibitor, such as inhibitors disclosed in PCT publication WO03/099773 or WO04/046092, or anti-ICAM-1 antibody or an oligonucleotide which prevents expression of ICAM, is administered in addition to a formulation of the present invention. In yet another embodiment, an additional active ingredient (e.g., an anti-inflammatory compound, such as sulfasalazine, azathioprine, 6-mercaptopurine, 5-aminosalicylic acid containing anti-inflammatories, another non-steroidal anti-inflammatory compound, a steroidal anti-inflammatory compound, or antibiotics commonly administered for control of IBD (e.g. ciprofloxacin, metronidazole), or another biologic agent (e.g. TNF alpha antagonists) can be administered in conjunction with a formulation of the present invention. In some embodiments, antibiotics are administered at the start of treatment with the anti-α4β7 antibody. In some embodiments, the antibiotics are metronidazole or ciprofloxacin. In some embodiments, the antibiotic is administered at day 1 of treatment with an anti-α4β7 antibody. In further embodiments, the antibiotic is administered for the first 2 weeks, first 3 weeks, first 4 weeks, first 5 weeks, first 6 weeks or first 7 weeks of treatment with the an anti-α4β7 antibody. In an embodiment, the dose of the co-administered medication can be decreased over time during the period of treatment by the formulation comprising the anti-α4β7 antibody. For example, a patient being treated with a steroid (e.g. prednisone, prednisolone) at the beginning, or prior to, treating with the anti-α4β7 antibody formulation would undergo a regimen of decreasing doses of steroid beginning as early as 6 weeks of treatment with the anti-α4β7 antibody formulation. The steroid dose will be reduced by about 25% within 4-8 weeks of initiating tapering, by 50% at about 8-12 weeks and 75% at about 12-16 weeks of tapering during treatment with the anti-α4β7 antibody formulation. In one aspect, by about 16-24 weeks of treatment with the anti-α4β7 antibody formulation, the steroid dose can be eliminated. In another example, a patient being treated with an anti-inflammatory compound, such as 6-mercaptopurine at the beginning, or prior to, treating with the anti-α4β7 antibody formulation would undergo a regimen of decreasing doses of anti-inflammatory compound similar to the tapering regimen for steroid dosing as noted above.

In one embodiment, the method comprises administering an effective amount of a formulation of the invention to a patient. If the formulation is in a solid, e.g., dry state, the process of administration can comprise a step of converting the formulation to a liquid state. In one aspect, a dry formulation can be reconstituted, e.g., by a liquid as described above, for use in injection, e.g. intravenous, intramuscular or subcutaneous injection. In another aspect, a solid or dry formulation can be administered topically, e.g., in a patch, cream, aerosol or suppository.

The α4β7 antagonist, which is an anti-α4β7 antibody, can bind to an epitope on the α4 chain (e.g., humanized MAb 21.6 (Bendig et al., U.S. Pat. No. 5,840,299), on the β7 chain (e.g., FIB504 or a humanized derivative (e.g., Fong et al., U.S. Pat. No. 7,528,236)), or to a combinatorial epitope formed by the association of the α4 chain with the β7 chain. AMG-181 or other antibodies described in US 2010/0254975 are anti-α4β7 antibodies. In one aspect, the antibody binds a combinatorial epitope on the α4β7 complex, but does not bind an epitope on the α4 chain or the β7 chain unless the chains are in association with each other. The association of α4 integrin with β7 integrin can create a combinatorial epitope for example, by bringing into proximity residues present on both chains which together comprise the epitope or by conformationally exposing on one chain, e.g., the α4 integrin chain or the β7 integrin chain, an epitopic binding site that is inaccessible to antibody binding in the absence of the proper integrin partner or in the absence of integrin activation. In another aspect, the anti-α4β7 antibody binds both the α4 integrin chain and the β7 integrin chain, and thus, is specific for the α4β7 integrin complex. Such antibodies can bind α4β7 but not bind α4β1, and/or not bind $α_Eβ_7$, for example. In another aspect, the anti-α4β7 antibody binds to the same or substantially the same epitope as the Act-1 antibody (Lazarovits, A. I. et al., *J. Immunol.*, 133(4): 1857-1862 (1984), Schweighoffer et al., *J. Immunol.*, 151(2): 717-729, 1993; Bednarczyk et al., *J. Biol. Chem.*, 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf Millennium Pharmaceuticals, Inc., 40 Lansdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the α4β7 antagonist is an anti-MAdCAM antibody (see e.g., U.S. Pat. No. 8,277,808, PF-00547659 or antibodies described in WO2005/067620), or an engineered form of a ligand, such as a MAdCAM-Fc chimera such as described in U.S. Pat. No. 7,803,904.

In one aspect, the anti-α4β7 antibody inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs are described in the PCT publication WO 96/24673, the entire teachings of which are incorporated herein by this reference. In another aspect, the anti-α4β7 antibody inhibits binding of α4β7 to MAdCAM (e.g., MAdCAM-1) and/or fibronectin without inhibiting the binding of VCAM.

In one aspect, the anti-α4β7 antibodies for use in the treatments are humanized versions of the mouse Act-1 antibody. Suitable methods for preparing humanized antibodies are well-known in the art. Generally, the humanized anti-α4β7 antibody will contain a heavy chain that contains the 3 heavy chain complementarity determining regions (CDRs, CDR1, SEQ ID NO:4, CDR2, SEQ ID NO:5 and CDR3, SEQ ID NO:6) of the mouse Act-1 antibody and suitable human heavy chain framework regions; and also contain a light chain that contains the 3 light chain CDRs (CDR1, SEQ ID NO:7, CDR2, SEQ ID NO:8 and CDR3, SEQ ID NO:9) of the mouse Act-1 antibody and suitable human light chain framework regions. The humanized Act-1 antibody can contain any suitable human framework regions, including consensus framework regions, with or without amino acid substitutions. For example, one or more of the framework amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), δ or a heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference. Treatment methods using anti-α4β7 integrin antibodies are described in publication nos. U.S. 2005/0095238, U.S. 2005/0095238, WO2012151248 and WO 2012/151247.

In one aspect, the anti-α4β7 antibody is vedolizumab. Vedolizumab IV (also called MLN0002, ENTYVIO™ or KYNTELES™) is a humanized antibody (Ig) G1 mAb directed against the human lymphocyte integrin α4β7. The α4β7 integrin mediates lymphocyte trafficking to GI mucosa and gut-associated lymphoid tissue (GALT) through adhesive interaction with mucosal addressin cell adhesion molecule-1 (MAdCAM-1), which is expressed on the endothelium of mesenteric lymph nodes and GI mucosa. Vedolizumab binds the α4β7 integrin, antagonizes its adherence to MAdCAM-1 and as such, impairs the migration of gut homing leukocytes into GI mucosa.

In another aspect, the humanized anti-α4β7 antibody for use in the treatment comprises a heavy chain variable region comprising amino acids 20 to 140 of SEQ ID NO:1, and a light chain variable region comprising amino acids 20 to 131 of SEQ ID NO:2 or amino acids 1 to 112 of SEQ ID NO:3. If desired, a suitable human constant region(s) can be present. For example, the humanized anti-α4β7 antibody can comprise a heavy chain that comprises amino acids 20 to 470 of SEQ ID NO:1 and a light chain comprising amino acids 1 to 219 of SEQ ID NO:3. In another example, the humanized anti-α4β7 antibody can comprise a heavy chain that comprises amino acids 20 to 470 of SEQ ID NO:1 and a light chain comprising amino acids 20 to 238 of SEQ ID NO:2. Vedolizumab is cataloged under Chemical Abstract Service (CAS, American Chemical Society) Registry number 943609-66-3).

Substitutions to the humanized anti-α4β7 antibody sequence can be, for example, mutations to the heavy and light chain framework regions, such as a mutation of isoleucine to valine on residue 2 of SEQ ID NO: 10; a mutation of methionine to valine on residue 4 of SEQ ID NO:10; a mutation of alanine to glycine on residue 24 of SEQ ID NO:11; a mutation of arginine to lysine at residue 38 of SEQ ID NO: 11; a mutation of alanine to arginine at residue 40 of SEQ ID NO: 11; a mutation of methionine to isoleucine on residue 48 of SEQ ID NO: 11; a mutation of isoleucine to leucine on residue 69 of SEQ ID NO:11; a mutation of arginine to valine on residue 71 of SEQ ID NO: 11; a mutation of threonine to isoleucine on residue 73 of SEQ ID NO: 11; or any combination thereof; and replacement of the heavy chain CDRs with the CDRs (CDR1, SEQ ID NO:4, CDR2, SEQ ID NO:5 and CDR3, SEQ ID NO:6) of the mouse Act-1 antibody; and replacement of the light chain CDRs with the light chain CDRs (CDR1, SEQ ID NO:7, CDR2, SEQ ID NO:8 and CDR3, SEQ ID NO:9) of the mouse Act-1 antibody.

The present invention provides, in a first aspect, a method for treating a patient, having a surgically implanted seton, suffering from fistulizing Crohn's disease with vedolizumab.

The method comprises the steps of administering two doses of vedolizumab to a patient suffering from IBD, wherein the second dose is administered about two weeks after the initial dose is administered to the patient; waiting a period of time of about four weeks; measuring the patient's serum concentration of vedolizumab; and administering one or more further doses of vedolizumab to the patient if the patient's serum concentration is at least about 8, about 10, about 12, about 14, about 17, about 20, about 25, about 30, about 35, or about 40 μg per ml. The patient's serum concentration may be between about 10 to 50, about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml.

Alternatively, at least one dose of vedolizumab may be administered to a patient suffering from fistulizing Crohn's disease, waiting at least about two weeks, or optionally, a period of two to five weeks, and then measuring the patient's serum concentration of vedolizumab and administering one or more further doses of vedolizumab to the patient if the patient's serum concentration is at least about 8, about 10, about 12, about 14, about 17, about 20, about 25, about 30, about 35, or about 40 μg per ml. The patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml.

The invention provides an anti-α4β7 antibody for use in for treating a patient having fistulizing Crohn's disease and having had surgical implantation of a seton in one or more fistula(e), the use comprising administering the anti-α4β7 antibody at least 2 weeks after surgical implantation and at 2, 6, 10, 14 and 22 weeks thereafter. The patient may have previously been administered a tumor necrosis factor-α (TNF) antagonist, such as an anti-TNF antibody and have had a recurrence of fistula(e) after such treatment. The use may further comprise administration of antibiotics during the early portion, e.g., on day 1 or during weeks 0 to 2, weeks 0 to 4, weeks 0 to 6, or weeks 1 to 8 of treatment with the anti-α4β7 antibody. The use may further comprise removal of the seton during 2 to 6 weeks, 4 to 10 weeks, 6 to 14 weeks, 6 to 20 weeks or 14 to 30 weeks after initial administration of the anti-α4β7 antibody. The use may further comprise administering the anti-α4β37 antibody every 2, 4, 6, 8 or 10 weeks after 22 weeks for maintenance of healed fistula(e). In some embodiments, the anti-α4β7 antibody is vedolizumab.

"Endoscopic remission" as used herein, refers to a condition with a low endoscopic score. The endoscopic score in ulcerative colitis can be the Mayo subscore. An example of a method to assess the endoscopic score in Crohn's disease is ileocolonoscopy. The endoscopic score in Crohn's disease can be the simple endoscopic score for Crohn's Disease (SES-CD). The SES-CD can include measures such as the size of ulcers, the amount of ulcerated surface, the amount of affected surface and whether and to what extent the alimentary canal is narrowed.

"Endoscopic response" as used herein, refers to a percentage decrease in an endoscopic score from baseline (e.g., at screening or just prior to initial dose). In Crohn's disease, endoscopic response can be assessed by a simple endoscopic score for Crohn's Disease (SES-CD).

In another reference to Crohn's disease, mucosal healing refers to an improvement in the amount or severity of wounding in mucosae, e.g., the digestive tract. For example, mucosal healing can refer to a decrease in the amount, size or severity of one or more than one ulcer in the digestive tract. In another example, mucosal healing refers to a decrease in one or more parameters selected from the group consisting of wall thickness, enhanced bowel wall contrast, mural edema, ulceration and perienteric vascularity. Such mucosal healing can be expressed as an SES-CD score, or a Magnetic Resonance Index of Activity (MaRIA) score. Complete mucosal healing in Crohn's disease includes absence of ulceration.

The "MaRIA score" is the sum of the scores, e.g., as measured by magnetic resonance enterography, of various mucosal healing parameters for each segment of colon and the terminal ileum (e.g., ileum, ascending colon, transverse colon, descending colon, sigmoid, and rectum).

"Corticosteroid (CS)-free remission" as used herein, refers to patients using oral corticosteroids at baseline who have discontinued corticosteroid use and are in clinical remission at week 52.

"European Quality of Life-5 Dimension (EQ-5D) visual analogue scale (VAS)" as used herein, refers to a questionnaire which is a validated (ahrq.gov/rice/eq5dproj.htm, "U.S. Valuation of the EuroQol EQ-5D™ Health States", accessed 8 Aug. 2012, Bastida et al. BMC Gastroenterology 10:26-(2010), Konig et al. European Journal of Gastroenterology & Hepatology 14:1205-1215 (2002)) instrument used to measure general health-related quality of life (HRQOL) in patients and includes five domains—mobility, self-care, usual activities, pain/discomfort, and anxiety/depression. Patients choose the level of health problems they currently have on each item as "None", "Moderate", or "Extreme" and are scored a 1, 2, or 3, respectively. A composite EQ-5D score can be calculated from the individual scores to assess overall HRQOL. The EQ-5D Visual Analog Scale (VAS) score is a self-assigned rating of overall health using a 20 cm visual, vertical scale, with a score of 0 as the worst and 100 as best possible health. The EQ-5D and EQ-5D VAS have been shown in many studies to be valid and reliable instruments for measuring HRQOL in patients with GI diseases. A decrease of ≥0.3 points in the EQ-5D score represents a clinically meaningful improvement in HRQOL for patients. An increase of greater than or equal to 7 points in the EQ-5D VAS score represents a clinically meaningful improvement in HRQOL for patients.

The "Inflammatory Bowel Disease Questionnaire" ((IBDQ) questionnaire" (Irvine Journal of Pediatric Gastroenterology & Nutrition 28:S23-27 (1999)) is used to assess quality of life in adult patients with inflammatory bowel disease, ulcerative colitis, or Crohn's Disease and includes 32 questions on four areas of HRQOL: Bowel Systems (10 questions), Emotional Function (12 questions), Social Function (5 questions), and Systemic Function (5 questions). Patients are asked to recall symptoms and quality of life from the last 2 weeks and rate each item on a 7-point Likert scale (higher scores equate to higher quality of life). A total IBDQ score is calculated by summing the scores from each domain; the total IBDQ score ranges from 32 to 224. An IBDQ total score greater than 170 is characteristic of the health related quality of life (HRQoL) of patients in remission.

As used herein, "induction therapy" is an initial stage of therapy, wherein a patient is administered a relatively intensive dosing regimen of a therapeutic agent. The therapeutic agent, e.g., antibody, is administered in a way that quickly provides an effective amount of the agent suitable for certain purposes, such as inducing immune tolerance to the agent or for inducing a clinical response and ameliorating disease symptoms (see WO 2012/151247 and WO 2012/151248, incorporated herein by reference).

As used herein, "maintenance therapy" is after induction therapy and is administered in a way that continues the response achieved by induction therapy with a stable level of therapeutic agent, e.g., antibody. A maintenance regimen can prevent return of symptoms or relapse of disease, e.g., IBD (see WO 2012/151247 and WO 2012/151248, incorporated herein by reference). A maintenance regimen can provide convenience to the patient, e.g., be a simple dosing regimen or require infrequent trips for treatment.

The invention will be more fully understood by reference to the following examples. They should not, however, be construed as limiting the scope of the invention. All literature and patent citations are incorporated herein by reference.

EXEMPLIFICATION

Example 1

This post hoc exploratory analysis evaluated the efficacy of vedolizumab in the subpopulation of patients with fistulising disease at baseline in the GEMINI 2 trial (NCT00783692). This was a phase 3, randomised, double-blind, PBO-controlled study consisting of separate induction and maintenance trials. In this study, 37% of patients had a history of fistulising disease and 15% had active draining fistula(e) at baseline (week 0).

In GEMINI 2, after 6 weeks of induction treatment with 2 doses of vedolizumab, 461 patients achieved a clinical response and received maintenance treatment with placebo, or vedolizumab 300 mg every 4 or 8 weeks (maintenance intent-to-treat [ITT] population). Fistula(e) closure, a pre-specified exploratory endpoint, was assessed at each visit (2-6 week intervals) until week 52. The number of patients achieving fistula(e) closure and mean time to fistula(e) closure were calculated.

At the start of the maintenance phase, 57 (12%) patients in the ITT population (N=461) had ≥1 draining fistula(e) at baseline, with 79% of fistula(e) located perianally. Among these patients, 44%-49% had failed prior anti-TNF therapy and 39%-54% had prior surgery for CD. By week 14, 28% of patients treated with vedolizumab had achieved fistula(e) closure versus 11.1% receiving vedolizumab/placebo (Table 1 and FIG. 1). This difference was maintained up to week 52. Kaplan-Meier probabilities of fistula(e) closure with vedolizumab were 29.2% and 33.4% at 6 and 12 months, respectively (FIG. 2). The hazard ratio for fistula(e) closure for the VDZ/VDZ treatment group was 2.54 (95% confidence interval [CI], 0.54-11.96).

These preliminary findings supporting the role of vedolizumab in the treatment of fistulising disease warrant further exploration in dedicated prospective studies in this population.

TABLE 1

Number of patients in the maintenance ITT population with at least 1 draining fistula at baseline who achieved fistula closure over time

| Week | VDZ/PBO*  n = 18 | VDZ (every 8 weeks)  n = 17 | VDZ (every 4 weeks)  n = 22 | VDZ (combined)  n = 39 |
|---|---|---|---|---|
| | Number 3 of patients achieving fistula closure (%) [95% CI] | | | |
| 6 | 4 (22.2) [6.4, 47.6] | 3 (17.6) [3.8, 43.4] | 3 (13.6) [2.9, 34.9] | 6 (15.4) [5.9, 30.5] |

TABLE 1-continued

Number of patients in the maintenance ITT population with at least 1 draining fistula at baseline who achieved fistula closure over time

| Week | VDZ/PBO*  n = 18 | VDZ (every 8 weeks)  n = 17 | VDZ (every 4 weeks)  n = 22 | VDZ (combined)  n = 39 |
|---|---|---|---|---|
| | Number 3 of patients achieving fistula closure (%) [95% CI] | | | |
| 14 | 2 (11.1) [1.4, 34.7] | 5 (29.4) [10.3, 56.0] | 6 (27.3) [10.7, 50.2] | 11 (28.2) [15.0, 44.9] |
| 26 | 3 (16.7) [3.6, 41.4] | 6 (35.3) [14.2, 61.7] | 5 (22.7) [7.8, 45.4] | 11 (28.2) [15.0, 44.9] |
| 52 | 2 (11.1) [1.4, 34.7] | 7 (41.2) [18.4, 67.1] | 5 (22.7) [7.8, 45.4] | 12 (30.8) [17.0, 47.6] |

*Patients in the placebo group received VDZ at week 0 and week 2 in the 6-week induction phase.
ITT, intent-to-treat; PBO, placebo.

Example 2

Most patients (approx. 88%) who entered GEMINI 2 did not have draining fistula(e) when they entered the study. Of those, 29% of VDZ/PBO-treated patients and 21% of VDZ/VDZ-treated patients had a history of fistulising disease. Over the course of the study, 3.2% of CD patients developed draining fistula(e). Patients who developed draining fistula(e) on study were more likely to have a history of fistulising disease compared with those who did not develop draining fistula(e). The median time with draining fistula(e) was 16 weeks (range 4-36) for VDZ/PBO-treated patients and 6 weeks (range 4-42) for those treated with VDZ/VDZ. Kaplan-Meier probabilities of developing draining fistula(e) with VDZ/VDZ treatment were 3.0% and 3.7% at 6 and 12 months, respectively, and 3.1% and 4.8%, respectively, with VDZ/PBO (FIG. 3). The hazard ratio for developing draining fistula(e) on study with VDZ/VDZ treatment was 0.77 (95% CI, 0.25, 2.43). Among VDZ/VDZ-treated patients who developed draining fistula(e), a greater percentage had a history of anti-TNF failure (88%), prior surgery for CD (75%) and higher median C-reactive protein (19.2 mg/L) compared with those who did not develop draining fistula(e) (51%, 35% and 8.8%, respectively); similar differences for VDZ/PBO-treated patients were not observed.

Example 3

A phase 4 randomized double-blind multicentre study will be done to evaluate the efficacy of 2 dose regimens of vedolizumab IV 300 mg, administered as a thirty minute infusion, over a 30-week treatment period (with the last dose at Week 22) in the healing of draining perianal fistula(e) in subjects with active Crohn's disease (CD). Subjects in both treatment groups entering the study will have had surgical seton placement as standard of care prior to enrolment in the study.

Approximately 126 CD subjects with moderately to severely active CD and 1 to 3 draining perianal fistula(e) of at least 2 weeks duration will be included. Subjects must have historically had an inadequate response with, lost response to, or been intolerant to either conventional therapy or a tumor necrosis factor-alpha (TNF-α) antagonist for their underlying CD to be eligible. Subjects will be randomized in a 1:1 ratio into 1 of 2 treatment groups:

Group 1: vedolizumab IV 300 mg dose at Week 0, 2, 6, 14, 22 and a placebo IV dose at Week 10

Group 2: vedolizumab IV 300 mg dose at Week 0, 2, 6, 10, 14, and 22

The study will consist of a 3-week screening period, a 30-week treatment period (with last dose at week 22), and an 18-week follow-up period following the last dose. The duration of the study from screening to 18 weeks post-treatment will be approximately 43 weeks for all subjects.

In both groups, setons may be removed after week 10 provided significant reduction in fistula(e) drainage and at the discretion of the investigator. All setons are recommended to be removed by week 14 and must be removed by week 22.

The primary objective in this study is to evaluate the proportion of subjects with fistula(e) healing at week 30 with 2 different dose regimens of vedolizumab IV 300 mg in subjects with fistulising CD. Fistula(e) healing at week 30 will be evaluated by magnetic resonance imaging (MRI) as compared to baseline. Clinical disease activity will be assessed by Perianal Disease Activity Index (PDAI) and Crohn's Disease Activity Index (CDAI) from Day 1 to weeks 2, 6, 10, 14, 22, and 30. Perianal pain will be evaluated at each visit. Quality of life measures, including Inflammatory Bowel Disease Questionnaire (IBDQ) and EuroQol-5 dimensions (EQ-5D) at weeks 14 and 30 will be compared to day 1. Fistula(e) draining will be assessed by comparing the number of pads used at week 30 compared to baseline.

The primary endpoint for this study is the proportion of subjects with a reduction of at least 50% from day 1 in number of draining fistula(e) at week 30 (where closed fistula(e) are no longer draining despite gentle finger compression). Secondary endpoints for the study are the proportion of subjects with 100% fistula(e) closing at week 30 (where all fistula(e) are no longer draining despite gentle finger compression); time to first fistula closing; time to last (100%) fistula closure; and duration of fistula(e) response (e.g., number of days with drainage). The time to first fistula closure and time to last fistula closure will be analysed by survival analysis procedures.

```
                            SEQUENCE LISTING

SEQ ID NO: 1
Met Gly Trp Ser Cys Ile Ile Leu Phe Leu Val Ala Thr Ala Thr
Gly
1               5                   10                  15

Val His Ser Gln Val Gln Leu Val Gln Ser Gly Ala Glu Val Lys
Lys
                20                  25                  30

Pro Gly Ala Ser Val Lys Val Ser Cys Lys Gly Ser Gly Tyr Thr
Phe
            35                  40                  45

Thr Ser Tyr Trp Met His Trp Val Arg Gln Ala Pro Gly Gln Arg
Leu
        50                  55                  60

Glu Trp Ile Gly Glu Ile Asp Pro Ser Glu Ser Asn Thr Asn Tyr
Asn
65                  70                  75                  80

Gln Lys Phe Lys Gly Arg Val Thr Leu Thr Val Asp Ile Ser Ala
Ser
                85                  90                  95

Thr Ala Tyr Met Glu Leu Ser Ser Leu Arg Ser Glu Asp Thr Ala
Val
                100                 105                 110

Tyr Tyr Cys Ala Arg Gly Gly Tyr Asp Gly Trp Asp Tyr Ala Ile
Asp
            115                 120                 125

Tyr Trp Gly Gln Gly Thr Leu Val Thr Val Ser Ser Ala Ser Thr
Lys
        130                 135                 140

Gly Pro Ser Val Phe Pro Leu Ala Pro Ser Ser Lys Ser Thr Ser
Gly
145                 150                 155
160

Gly Thr Ala Ala Leu Gly Cys Leu Val Lys Asp Tyr Phe Pro Glu
Pro
            165                 170                 175

Val Thr Val Ser Trp Asn Ser Gly Ala Leu Thr Ser Gly Val His
Thr
                180                 185                 190

Phe Pro Ala Val Leu Gln Ser Ser Gly Leu Tyr Ser Leu Ser Ser
Val
            195                 200                 205
```

```
Val Thr Val Pro Ser Ser Leu Gly Thr Gln Thr Tyr Ile Cys
Asn
        210                 215                 220

Val Asn His Lys Pro Ser Asn Thr Lys Val Asp Lys Lys Val Glu
Pro
225                 230                 235
240

Lys Ser Cys Asp Lys Thr His Thr Cys Pro Pro Cys Pro Ala Pro
Glu
                245                 250                 255

Leu Ala Gly Ala Pro Ser Val Phe Leu Phe Pro Pro Lys Pro Lys
Asp
                260                 265                 270

Thr Leu Met Ile Ser Arg Thr Pro Glu Val Thr Cys Val Val Val
Asp
            275                 280                 285

Val Ser His Glu Asp Pro Glu Val Lys Phe Asn Trp Tyr Val Asp
Gly
            290                 295                 300

Val Glu Val His Asn Ala Lys Thr Lys Pro Arg Glu Glu Gln Tyr
Asn
305                 310                 315
320

Ser Thr Tyr Arg Val Val Ser Val Leu Thr Val Leu His Gln Asp
Trp
                325                 330                 335

Leu Asn Gly Lys Glu Tyr Lys Cys Lys Val Ser Asn Lys Ala Leu
Pro
                340                 345                 350

Ala Pro Ile Glu Lys Thr Ile Ser Lys Ala Lys Gly Gln Pro Arg
Glu
                355                 360                 365

Pro Gln Val Tyr Thr Leu Pro Pro Ser Arg Asp Glu Leu Thr Lys
Asn
            370                 375                 380

Gln Val Ser Leu Thr Cys Leu Val Lys Gly Phe Tyr Pro Ser Asp
Ile
385                 390                 395
400

Ala Val Glu Trp Glu Ser Asn Gly Gln Pro Glu Asn Asn Tyr Lys
Thr
                405                 410                 415

Thr Pro Pro Val Leu Asp Ser Asp Gly Ser Phe Phe Leu Tyr Ser
Lys
                420                 425                 430

Leu Thr Val Asp Lys Ser Arg Trp Gln Gln Gly Asn Val Phe Ser
Cys
                435                 440                 445

Ser Val Met His Glu Ala Leu His Asn His Tyr Thr Gln Lys Ser
Leu
            450                 455                 460

Ser Leu Ser Pro Gly Lys
465                 470

SEQ ID NO: 2
Met Gly Trp Ser Cys Ile Ile Leu Phe Leu Val Ala Thr Ala Thr
Gly
1               5                   10                  15

Val His Ser Asp Val Val Met Thr Gln Ser Pro Leu Ser Leu Pro
```

SEQUENCE LISTING

```
Val
            20                  25                  30

Thr Pro Gly Glu Pro Ala Ser Ile Ser Cys Arg Ser Ser Gln Ser
Leu
            35                  40                  45

Ala Lys Ser Tyr Gly Asn Thr Tyr Leu Ser Trp Tyr Leu Gln Lys
Pro
            50                  55                  60

Gly Gln Ser Pro Gln Leu Leu Ile Tyr Gly Ile Ser Asn Arg Phe
Ser
 65                 70                  75                  80

Gly Val Pro Asp Arg Phe Ser Gly Ser Gly Ser Gly Thr Asp Phe
Thr
                    85                  90                  95

Leu Lys Ile Ser Arg Val Glu Ala Glu Asp Val Gly Val Tyr Tyr
Cys
            100                 105                 110

Leu Gln Gly Thr His Gln Pro Tyr Thr Phe Gly Gln Gly Thr Lys
Val
            115                 120                 125

Glu Ile Lys Arg Thr Val Ala Ala Pro Ser Val Phe Ile Phe Pro
Pro
        130                 135                 140

Ser Asp Glu Gln Leu Lys Ser Gly Thr Ala Ser Val Val Cys Leu
Leu
145                 150                 155
160

Asn Asn Phe Tyr Pro Arg Glu Ala Lys Val Gln Trp Lys Val Asp
Asn
                165                 170                 175

Ala Leu Gln Ser Gly Asn Ser Gln Glu Ser Val Thr Glu Gln Asp
Ser
            180                 185                 190

Lys Asp Ser Thr Tyr Ser Leu Ser Ser Thr Leu Thr Leu Ser Lys
Ala
            195                 200                 205

Asp Tyr Glu Lys His Lys Val Tyr Ala Cys Glu Val Thr His Gln
Gly
        210                 215                 220

Leu Ser Ser Pro Val Thr Lys Ser Phe Asn Arg Gly Glu Cys
225                 230                 235

SEQ ID NO: 3
Asp Val Val Met Thr Gln Ser Pro Leu Ser Leu Pro Val Thr Pro
Gly
 1              5                  10                  15

Glu Pro Ala Ser Ile Ser Cys Arg Ser Ser Gln Ser Leu Ala Lys
Ser
            20                  25                  30

Tyr Gly Asn Thr Tyr Leu Ser Trp Tyr Leu Gln Lys Pro Gly Gln
Ser
            35                  40                  45

Pro Gln Leu Leu Ile Tyr Gly Ile Ser Asn Arg Phe Ser Gly Val
Pro
            50                  55                  60

Asp Arg Phe Ser Gly Ser Gly Ser Gly Thr Asp Phe Thr Leu Lys
Ile
 65                 70                  75                  80

Ser Arg Val Glu Ala Glu Asp Val Gly Val Tyr Tyr Cys Leu Gln
```

SEQUENCE LISTING

```
Gly
                85                  90                  95
Thr His Gln Pro Tyr Thr Phe Gly Gln Gly Thr Lys Val Glu Ile
Lys
            100                 105                 110
Arg Ala Asp Ala Ala Pro Ser Val Phe Ile Phe Pro Pro Ser Asp
Glu
            115                 120                 125
Gln Leu Lys Ser Gly Thr Ala Ser Val Val Cys Leu Leu Asn Asn
Phe
        130                 135                 140
Tyr Pro Arg Glu Ala Lys Val Gln Trp Lys Val Asp Asn Ala Leu
Gln
145                 150                 155
160
Ser Gly Asn Ser Gln Glu Ser Val Thr Glu Gln Asp Ser Lys Asp
Ser
                165                 170                 175
Thr Tyr Ser Leu Ser Ser Thr Leu Thr Leu Ser Lys Ala Asp Tyr
Glu
            180                 185                 190
Lys His Lys Val Tyr Ala Cys Glu Val Thr His Gln Gly Leu Ser
Ser
            195                 200                 205
Pro Val Thr Lys Ser Phe Asn Arg Gly Glu Cys
        210                 215

SEQ ID NO: 4
Ser Tyr Trp Met His
1               5

SEQ ID NO: 5
Glu Ile Asp Pro Ser Glu Ser Asn Thr Asn Tyr Asn Gln Lys Phe
Lys
1               5                   10                  15
Gly

SEQ ID NO: 6
Gly Gly Tyr Asp Gly Trp Asp Tyr Ala Ile Asp Tyr
1               5                   10

SEQ ID NO: 7
Arg Ser Ser Gln Ser Leu Ala Lys Ser Tyr Gly Asn Thr Tyr Leu
Ser
1               5                   10                  15

SEQ ID NO: 8
Gly Ile Ser Asn Arg Phe Ser
1               5

SEQ ID NO: 9
Leu Gln Gly Thr His Gln Pro Tyr Thr
1               5

SEQ ID NO: 10
Asp Ile Val Met Thr Gln Ser Pro Leu Ser Leu Pro Val Thr Pro
Gly
1               5                   10                  15
Glu Pro Ala Ser Ile Ser Cys Arg Ser Ser Gln Ser Leu Leu His
Ser
            20                  25                  30
Asn Gly Tyr Asn Tyr Leu Asp Trp Tyr Leu Gln Lys Pro Gly Gln
Ser
        35                  40                  45
Pro Gln Leu Leu Ile Tyr Leu Gly Ser Asn Arg Ala Ser Gly Val
Pro
```

SEQUENCE LISTING

```
                    50                  55                  60
Asp Arg Phe Ser Gly Ser Gly Ser Gly Thr Asp Phe Thr Leu Lys
Ile
 65                  70                  75                  80
Ser Arg Val Glu Ala Glu Asp Val Gly Val Tyr Tyr Cys Met Gln
Ala
                    85                  90                  95
Leu Gln Thr Pro Gln Thr Phe Gly Gln Gly Lys Val Glu Ile Lys
                   100                 105                 110

SEQ ID NO: 11
Gln Val Gln Leu Val Gln Ser Gly Ala Glu Val Lys Lys Pro Gly
Ala
 1                   5                  10                  15
Ser Val Lys Val Ser Cys Lys Ala Ser Gly Tyr Thr Phe Thr Ser
Tyr
                    20                  25                  30
Ala Met His Trp Val Arg Gln Ala Pro Gly Gln Arg Leu Glu Trp
Met
                    35                  40                  45
Gly Trp Ile Asn Ala Gly Asn Gly Asn Thr Lys Tyr Ser Gln Lys
Phe
                    50                  55                  60
Gln Gly Arg Val Thr Ile Thr Arg Asp Thr Ser Ala Ser Thr Ala
Tyr
 65                  70                  75                  80
Met Glu Leu Ser Ser Leu Arg Ser Glu Asp Thr Ala Val Tyr Tyr
Cys
                    85                  90                  95
Ala Arg Gly Gly Tyr Tyr Gly Ser Gly Ser Asn Tyr Trp Gly Gln
Gly
                   100                 105                 110
Thr Leu Val Thr Val Ser Ser
                   115
```

The invention claimed is:

1. A method for treating a human patient suffering from perianal fistulizing Crohn's disease, the method comprising
identifying a human patient having fistulizing moderately to severely active Crohn's disease and who had a lack of an adequate response with, loss response to, or was intolerant to treatment with a tumor necrosis factor-alpha antagonist and has at least one perianal draining fistula(e),
administering a humanized antibody having binding specificity for human α4β7 integrin to the human patient,
wherein the humanized antibody is administered to the human patient according to the following dosing regimen:
a. an initial dose of 300 mg of the humanized antibody as an intravenous infusion;
b. followed by a second subsequent dose of 300 mg of the humanized antibody as an intravenous infusion at about two weeks after the initial dose;
c. followed by a third subsequent dose of 300 mg of the humanized antibody as an intravenous infusion at about six weeks after the initial dose;
d. followed by a fourth and subsequent doses of 300 mg of the humanized antibody as an intravenous infusion every eight weeks after the third subsequent dose of the humanized antibody as needed; and
e. administering antibiotics during weeks 0 to 6 of treatment with the humanized antibody;
wherein at least 50% of the perianal draining fistulae are closed 30 weeks after the initial dose;
wherein the Perianal Disease Activity Index (PDAI) score of the patient is reduced by at least 3 points from baseline; and
wherein the humanized antibody comprises an antigen binding region of nonhuman origin and at least a portion of an antibody of human origin, wherein the humanized antibody has binding specificity for the α4β7 complex, wherein the antigen-binding region comprises the CDRs:
Light chain: CDR1 SEQ ID NO:7
  CDR2 SEQ ID NO:8 and
  CDR3 SEQ ID NO:9; and
Heavy chain: CDR1 SEQ ID NO:4
  CDR2 SEQ ID NO:5 and
  CDR3 SEQ ID NO:6.

2. The method of claim 1, wherein the human patient has a seton that was surgically placed prior to administration of the antibody.

3. The method of claim 1, wherein said human patient further has an abdominal fistula(e), an enterocutaneous fistula(e), or a combination thereof.

4. The method of claim 1, wherein perianal fistula(e) closure is measured by magnetic resonance imaging (MRI) assessment.

5. The method of claim 1, wherein 100% of the draining perianal fistula(e) are closed by the treatment.

6. The method of claim 1, wherein the patient further had a lack of an adequate response with, loss response to, or was intolerant to treatment with an azathioprine, 6-mercaptopurine, or methotrexate.

7. The method of claim 1, wherein the humanized antibody is reconstituted from a lyophilized formulation.

8. The method of claim 1, wherein the human patient further had a lack of an adequate response with or loss of response to a corticosteroid.

9. The method of claim 1, wherein the humanized antibody has a heavy chain variable region sequence of amino acids 20 to 140 of SEQ ID NO:1 and a light chain variable region sequence of amino acids 20 to 131 of SEQ ID NO:2.

10. The method of claim 1, wherein the humanized antibody is vedolizumab.

11. A method for treating a human patient suffering from perianal fistulizing Crohn's disease, wherein the method comprises identifying a human patient having fistulizing moderately to severely active Crohn's disease and has at least one perianal draining fistula(e), administering a humanized antibody having binding specificity for human α4β7 integrin to the human patient, wherein the humanized antibody is administered to the human patient according to the following dosing regimen:

a. an initial dose of 300 mg of the humanized antibody as an intravenous infusion;

b. followed by a second subsequent dose of 300 mg of the humanized antibody as an intravenous infusion at about two weeks after the initial dose;

c. followed by a third subsequent dose of 300 mg of the humanized antibody as an intravenous infusion at about six weeks after the initial dose;

d. followed by a fourth and subsequent doses of 300 mg of the humanized antibody as an intravenous infusion every eight weeks after the third subsequent dose of the humanized antibody as needed; and e. administering antibiotics during weeks 0 to 6 of treatment with the humanized antibody;

wherein at least 50% of the perianal draining fistulae are closed 30 weeks after the initial dose;

wherein the perianal fistula(e) closure is measured by magnetic resonance imaging (MRI) assessment;

wherein the human patient had a lack of an adequate response with, loss response to, or was intolerant to treatment with a tumor necrosis factor-alpha antagonist; and wherein the humanized antibody comprises an antigen binding region of nonhuman origin and at least a portion of an antibody of human origin, wherein the humanized antibody has binding specificity for the α4β7 complex, wherein the antigen-binding region comprises the CDRs:

Light chain: CDR1 SEQ ID NO:7
CDR2 SEQ ID NO:8 and
CDR3 SEQ ID NO:9; and
Heavy chain: CDR1 SEQ ID NO:4 CDR2 SEQ ID NO:5 and CDR3 SEQ ID NO:6.

12. The method of claim 11, wherein the human patient has a seton that was surgically placed prior to administration of the antibody.

13. The method according to claim 11, wherein said treatment is further measured by a PDAI score or a CDAI score of the human patient.

14. The method of claim 11, wherein the humanized antibody has a heavy chain variable region sequence of amino acids 20 to 140 of SEQ ID NO:1 and a light chain variable region sequence of amino acids 20 to 131 of SEQ ID NO:2.

15. The method of claim 11, wherein the humanized antibody is vedolizumab.

16. A method for treating a human patient suffering from perianal fistulizing Crohn's disease, wherein the method comprises identifying a human patient having fistulizing moderately to severely active Crohn's disease and who had a lack of an adequate response with, loss response to, or was intolerant to treatment with a tumor necrosis factor-alpha antagonist and has at least one perianal draining fistula(e), administering to the human patient a humanized antibody having binding specificity for human α4β7, wherein the humanized antibody is administered to the human patient according to the following dosing regimen:

a. an initial dose of 300 mg of the humanized antibody as an intravenous infusion;

b. followed by a second subsequent dose of 300 mg of the humanized antibody as an intravenous infusion at about two weeks after the initial dose;

c. followed by a third subsequent dose of 300 mg of the humanized antibody as an intravenous infusion at about six weeks after the initial dose;

d. followed by a fourth subsequent dose of 300 mg of the humanized antibody as an intravenous infusion at about 14 weeks after the initial dose;

e. followed by a fifth subsequent dose and subsequent doses of 300 mg of the humanized antibody as an intravenous infusion every eight weeks after the fourth subsequent dose of the humanized antibody as needed; and f. administering antibiotics during weeks 0 to 6 of treatment with the humanized antibody;

wherein the human patient has a seton that was surgically placed prior to administration of the antibody, wherein at least 50% of the perianal draining fistulae are closed 30 weeks after the initial dose; and further wherein the humanized antibody comprises an antigen binding region of nonhuman origin and at least a portion of an antibody of human origin, wherein the humanized antibody has binding specificity for the α4β7 complex, wherein the antigen-binding region comprises the CDRs:

Light chain: CDR1 SEQ ID NO:7
CDR2 SEQ ID NO:8 and
CDR3 SEQ ID NO:9; and
Heavy chain: CDR1 SEQ ID NO:4
CDR2 SEQ ID NO:5 and
CDR3 SEQ ID NO:6.

17. The method of claim 16, wherein perianal fistula(e) closure is measured by magnetic resonance imaging (MRI) assessment.

18. The method of claim 16, wherein the humanized antibody has a heavy chain variable region sequence of amino acids 20 to 140 of SEQ ID NO:1 and a light chain variable region sequence of amino acids 20 to 131 of SEQ ID NO:2.

19. The method of claim 16, wherein the humanized antibody is vedolizumab.

20. The method of claim 16, wherein the seton is removed at or after week 14.

* * * * *